US012651312B2

(12) United States Patent
    Okumura

(10) Patent No.:    US 12,651,312 B2
(45) Date of Patent:      Jun. 9, 2026

(54) IMAGE PROCESSING DEVICE, METHOD FOR OPERATING IMAGE PROCESSING DEVICE, AND PROGRAM FOR OPERATING IMAGE PROCESSING DEVICE

(71) Applicant: FUJIFILM Corporation, Tokyo (JP)

(72) Inventor: Yukari Okumura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 167 days.

(21) Appl. No.: 18/178,434

(22) Filed: Mar. 3, 2023

(65) Prior Publication Data

US 2023/0206397 A1     Jun. 29, 2023

Related U.S. Application Data

(63) Continuation of application No. PCT/JP2021/023596, filed on Jun. 22, 2021.

(30) Foreign Application Priority Data

Sep. 29, 2020    (JP) ................................. 2020-163981

(51) Int. Cl.
    *G06T 3/4053*      (2024.01)
    *A61B 6/00*      (2006.01)
    (Continued)

(52) U.S. Cl.
    CPC ............ *G06T 3/4053* (2013.01); *A61B 6/463* (2013.01); *A61B 6/5217* (2013.01); *G06T 1/00* (2013.01);
    (Continued)

(58) Field of Classification Search
    None
    See application file for complete search history.

(56) References Cited

U.S. PATENT DOCUMENTS

2006/0061570 A1    3/2006   Cheryauka et al.
2015/0093009 A1    4/2015   Woods et al.
             (Continued)

FOREIGN PATENT DOCUMENTS

JP      2006-087921 A     4/2006
JP      2009276163 A   *   11/2009
             (Continued)

OTHER PUBLICATIONS

An Office Action; "Notice of Reasons for Refusal," mailed by the Japanese Patent Office on Nov. 21, 2023, which corresponds to Japanese Patent Application No. 2022-553471 and is related to U.S. Appl. No. 18/178,434; with English language translation.
             (Continued)

*Primary Examiner* — Yi Wang
(74) *Attorney, Agent, or Firm* — Studebaker Brackett PLLC

(57)             ABSTRACT

An image processing device includes a processor and a memory that is connected to or provided in the processor. The processor acquires a plurality of tomographic images which indicate a plurality of tomographic planes of an object, respectively, and have a first resolution, sets a partial region of the tomographic image as a target region in a case in which an operation instruction related to interpretation is received from a user, performs a process of converting a resolution into a second resolution higher than the first resolution only on the target region to generate a high-resolution partial image of the target region, and displays the high-resolution partial image.

9 Claims, 27 Drawing Sheets

(51) Int. Cl.

| | |
|---|---|
| *A61B 6/46* | (2024.01) |
| *G06T 1/00* | (2006.01) |
| *G06T 7/11* | (2017.01) |
| *G06T 12/20* | (2026.01) |
| *G06T 12/30* | (2026.01) |

(52) U.S. Cl.
CPC ................ *G06T 7/11* (2017.01); *G06T 12/20* (2026.01); *G06T 12/30* (2026.01); *G06T 2200/28* (2013.01); *G06T 2207/10072* (2013.01); *G06T 2207/20104* (2013.01); *G06T 2207/20212* (2013.01); *G06T 2207/30068* (2013.01); *G06T 2207/30096* (2013.01)

(56) References Cited

U.S. PATENT DOCUMENTS

| | | | |
|---|---|---|---|
| 2015/0201890 A1 | 7/2015 | Maidment et al. | |
| 2016/0073986 A1 | 3/2016 | Saito et al. | |
| 2020/0211239 A1 | 7/2020 | Ng et al. | |

FOREIGN PATENT DOCUMENTS

| | | | |
|---|---|---|---|
| JP | 2010-011964 A | 1/2010 | |
| JP | 2015-006324 A | 1/2015 | |

OTHER PUBLICATIONS

International Search Report issued in PCT/JP2021/023596; mailed Aug. 3, 2021.

International Preliminary Report on Patentability (Chapter I) and Written Opinion of the International Searching Authority issued in PCT/JP2021/023596; issued Mar. 28, 2023.

The extended European search report issued by the European Patent Office on Feb. 12, 2024, which corresponds to European Patent Application No. 2174836.6-1210 and is related to U.S. Appl. No. 18/178,434.

The European Office Action issued by the European Patent Office on Oct. 7, 2025, which corresponds to European Patent Application No. 21874836.6 and is related to U.S. Appl. No. 18/178,434.

* cited by examiner

Figure 25:
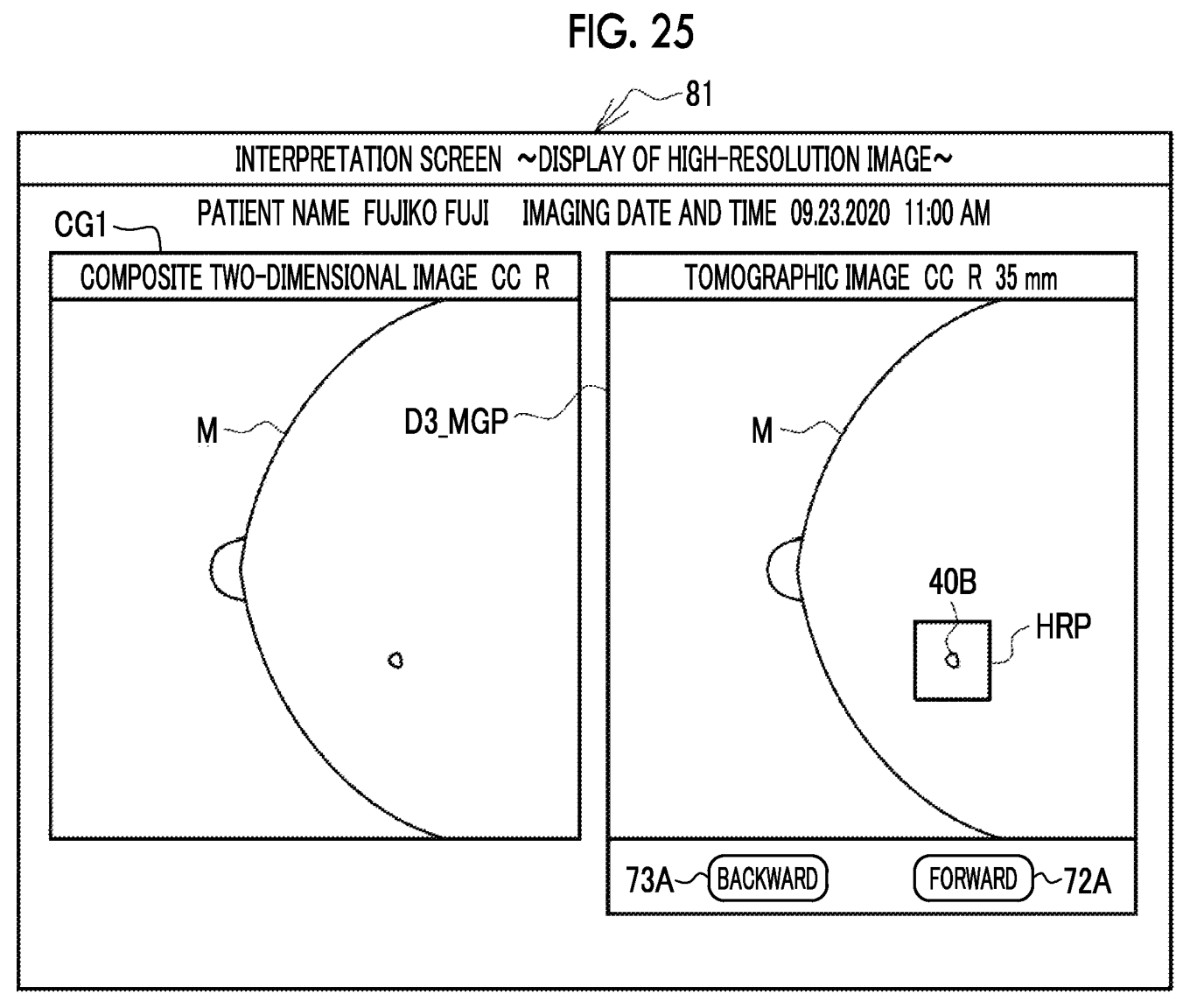

INTERPRETATION SCREEN ~DISPLAY OF HIGH-RESOLUTION IMAGE~

PATIENT NAME  FUJIKO FUJI    IMAGING DATE AND TIME  09.23.2020  11:00 AM

CG1

COMPOSITE TWO-DIMENSIONAL IMAGE  CC  R

M

D3_MGP

TOMOGRAPHIC IMAGE  CC  R  35 mm

M

40B

HRP

73A   BACKWARD     FORWARD   72A

IMAGE PROCESSING DEVICE, METHOD FOR OPERATING IMAGE PROCESSING DEVICE, AND PROGRAM FOR OPERATING IMAGE PROCESSING DEVICE

CROSS-REFERENCE TO RELATED APPLICATION

This application is a continuation application of International Application No. PCT/JP2021/023596, filed Jun. 22, 2021, the disclosure of which is incorporated herein by reference in its entirety. Further, this application claims priority from Japanese Patent Application No. 2020-163981 filed on Sep. 29, 2020, the disclosure of which is incorporated herein by reference in its entirety.

BACKGROUND

1. Technical Field

The technology of the present disclosure relates to an image processing device, a method for operating an image processing device, and a program for operating an image processing device.

2. Description of the Related Art

A technique for obtaining a plurality of tomographic images in any tomographic planes of an object, such as tomosynthesis imaging which irradiates the object with radiation at a plurality of different irradiation angles, is known. According to the tomographic images, a structure of the object which extends in a depth direction in which the tomographic planes are arranged can be separately drawn in each tomographic image. Therefore, it is possible to draw a structure of interest, such as a lesion, which is difficult to draw in a two-dimensional image which is a simple projection image of the object.

For example, US2015/0201890A discloses a technique that generates a tomographic image in which the resolution of the entire region has been increased (hereinafter, simply referred to as a high-resolution tomographic image) in order to support detailed interpretation of the tomographic image.

SUMMARY

For example, in a case in which the tomographic image obtained by the tomosynthesis imaging is interpreted, a radiologist does not interpret the tomographic image immediately, but interprets the two-dimensional image first. Then, a lesion portion is roughly estimated in the two-dimensional image. Then, a tomographic image of a tomographic plane in which the estimated lesion is likely to be present is searched for, and the searched tomographic image is interpreted in detail. The reason for this interpretation procedure is that it is inefficient to interpret a plurality of tomographic images at random without any purpose at first.

According to the technique disclosed in US2015/0201890A, the lesion is expressed in high definition in the high-resolution tomographic image, which facilitates interpretation. However, it takes time to generate the high-resolution tomographic image. Therefore, in a case in which the generation of the high-resolution tomographic image is started in response to an instruction to display the high-resolution tomographic image from the radiologist, there is a concern that a time lag which is long enough to cause a problem in practice will occur between the input of the instruction and the actual display of the high-resolution tomographic image.

As a method for solving the problem of the display time lag, a method is considered which generates the high-resolution tomographic images of all tomographic planes in advance, stores the high-resolution tomographic images in a storage, and reads the high-resolution tomographic images from the storage in a case in which the high-resolution tomographic images are displayed. However, this method causes another problem that pressure is applied to the capacity of the storage by the high-resolution tomographic images having a relatively large amount of data.

An embodiment according to the technology of the present disclosure provides an image processing device, a method for operating an image processing device, and a program for operating an image processing device that can shorten the time required for displaying high-resolution tomographic images without increasing the resolution of the tomographic images of all tomographic planes in advance.

According to the technology of the present disclosure, there is provided an image processing device comprises: a processor; and a memory that is connected to or provided in the processor. The processor acquires a plurality of tomographic images which indicate a plurality of tomographic planes of an object, respectively, and have a first resolution, sets a partial region of the tomographic image as a target region in a case in which an operation instruction related to interpretation is received from a user, performs a process of converting a resolution into a second resolution higher than the first resolution only on the target region to generate a high-resolution partial image of the target region, and displays the high-resolution partial image.

Preferably, the processor receives, as the operation instruction, an instruction to input a designated region in a two-dimensional image which is a projection image of the object and sets the target region on the basis of the designated region.

Preferably, the processor performs a process of detecting a structure of interest in the designated region and sets a region including the structure of interest in the tomographic image as the target region in a case in which the structure of interest is detected.

Preferably, the processor performs a process of detecting a structure of interest in the designated region and sets a region corresponding to the designated region in a tomographic image of a predetermined set tomographic plane as the target region in a case in which the structure of interest is not detected.

Preferably, the object is a breast, and the structure of interest is at least one of a tumor, a spicula, a calcification, or a linear structure.

Preferably, the plurality of tomographic images are obtained by tomosynthesis imaging which irradiates an object with radiation at a plurality of different irradiation angles, and the two-dimensional image is either a simple two-dimensional image obtained by simple imaging which emits the radiation, with a radiation source facing a radiation detector, or a composite two-dimensional image which is a pseudo simple two-dimensional image obtained by combining the plurality of tomographic images using a composite image generation technique.

Preferably, the processor performs a process of detecting a structure of interest in a two-dimensional image which is a projection image of the object in a case in which a first display instruction for the two-dimensional image is received as the operation instruction and sets a region including the structure of interest detected in the tomographic image as the target region in a case in which the structure of interest is detected.

Preferably, the object is a breast, and the structure of interest is at least one of a tumor, a spicula, a calcification, or a linear structure.

Preferably, the plurality of tomographic images are obtained by tomosynthesis imaging which irradiates an object with radiation at a plurality of different irradiation angles, and the two-dimensional image is either a simple two-dimensional image obtained by simple imaging which emits the radiation, with a radiation source facing a radiation detector, or a composite two-dimensional image which is a pseudo simple two-dimensional image obtained by combining the plurality of tomographic images using a composite image generation technique.

Preferably, the processor applies a super-resolution method to a process of converting the first resolution into the second resolution.

Preferably, in a case in which a plurality of the target regions are set and a plurality of the high-resolution partial images are generated, the processor generates the high-resolution partial image whenever a second display instruction for the high-resolution partial image is received from a user.

Preferably, in a case in which a plurality of the target regions are set and a plurality of the high-resolution partial images are generated, the processor generates the high-resolution partial images of the plurality of target regions before a second display instruction for the high-resolution partial image is received from a user.

Preferably, the processor displays the high-resolution partial image separately from the tomographic image in which the target region is set.

Preferably, the processor combines the high-resolution partial image with an enlarged image obtained by simply enlarging a region other than the target region in the tomographic image, in which the target region is set, according to the second resolution and displays the enlarged image.

Preferably, the processor displays the high-resolution partial image prior to the tomographic image in which the target region is not set.

Preferably, in a case in which a plurality of the target regions are set and a plurality of the high-resolution partial images are generated, the processor first displays one high-resolution partial image satisfying a predetermined display condition among the plurality of high-resolution partial images.

Preferably, in a case in which a second display instruction for the high-resolution partial image is received through a graphical user interface after the operation instruction is received, the processor displays the high-resolution partial image.

According to the technology of the present disclosure, there is provided a method for operating an image processing device. The method comprises: acquiring a plurality of tomographic images which indicate a plurality of tomographic planes of an object, respectively, and have a first resolution; setting a partial region of the tomographic image as a target region in a case in which an operation instruction related to interpretation is received from a user; performing a process of converting a resolution into a second resolution higher than the first resolution only on the target region to generate a high-resolution partial image of the target region; and displaying the high-resolution partial image.

According to the technology of the present disclosure, there is provided a program for operating an image processing device. The program causes a computer to execute a process comprising: acquiring a plurality of tomographic images which indicate a plurality of tomographic planes of an object, respectively, and have a first resolution; setting a partial region of the tomographic image as a target region in a case in which an operation instruction related to interpretation is received from a user; performing a process of converting a resolution into a second resolution higher than the first resolution only on the target region to generate a high-resolution partial image of the target region; and displaying the high-resolution partial image.

According to the technology of the present disclosure, it is possible to provide an image processing device, a method for operating an image processing device, and a program for operating an image processing device that can shorten the time required for displaying high-resolution tomographic images without increasing the resolution of the tomographic images of all tomographic planes.

BRIEF DESCRIPTION OF THE DRAWINGS

Exemplary embodiments according to the technique of the present disclosure will be described in detail based on the following figures, wherein:

FIG. 17 is a diagram illustrating display conditions and a display order in a case in which the structure of interest is detected from the designated region, FIG. 18 is a diagram illustrating display conditions and a display order in a case in which the structure of interest is not detected from the designated region, FIG. 24 is a diagram illustrating a process of combining the high-resolution partial image with a simply enlarged tomographic image in which a region other than the target region has been simply enlarged, FIG. 25 is a diagram illustrating a screen including a simply enlarged tomographic image with which the high-resolution partial image illustrated in FIG. 24 has been combined.

DETAILED DESCRIPTION

First Embodiment

Figure 1:
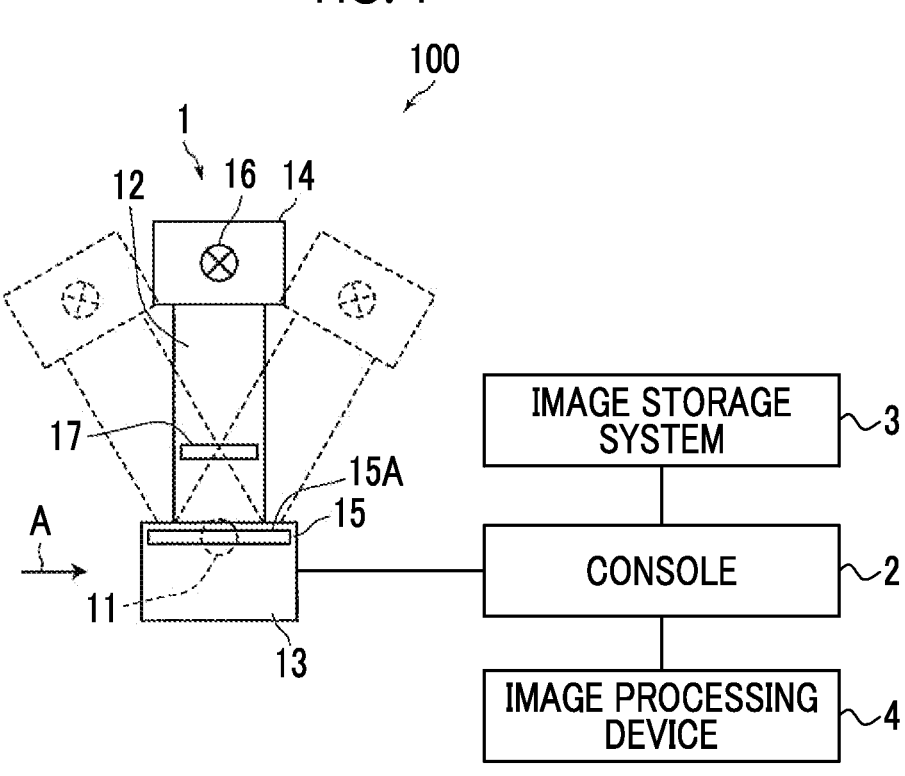
FIG. 1 is a diagram schematically illustrating a configuration of a radiography system to which an image processing device according to the present disclosure is applied.
Figure 2:
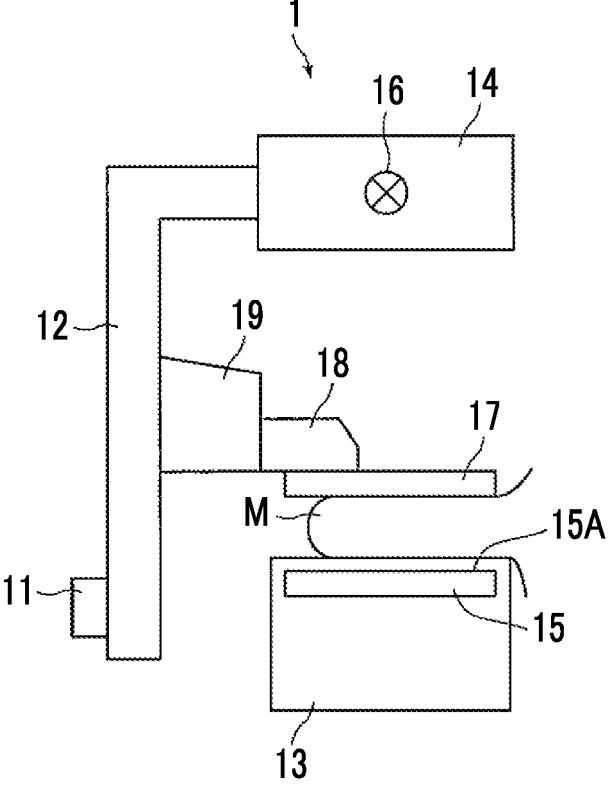
FIG. 2 is a diagram illustrating a mammography apparatus as viewed from a direction of an arrow A in FIG. 1.

Hereinafter, embodiments of the present disclosure will be described with reference to the drawings. FIG. 1 is a diagram schematically illustrating a configuration of a radiography system 100 to which an image processing device 4 according to an embodiment of the present disclosure is applied, and FIG. 2 is a diagram illustrating a mammography apparatus in the radiography system 100 as viewed from a direction of an arrow A in FIG. 1. As illustrated in FIG. 1, the radiography system 100 according to this embodiment images a breast M, which is an example of an "object" according to the technology of the present disclosure, at a plurality of radiation source positions to acquire a plurality of radiographic images, that is, a plurality of projection images, in order to perform tomosynthesis imaging on the breast M to generate tomographic images of the breast M. The radiography system 100 according to this embodiment comprises a mammography apparatus 1, a console 2, an image storage system 3, and the image processing device 4.

The mammography apparatus 1 comprises an arm portion 12 that is connected to a base (not illustrated) by a rotation shaft 11. An imaging table 13 is attached to one end of the arm portion 12, and a radiation emitting unit 14 is attached to the other end of the arm portion 12 to face the imaging table 13. The arm portion 12 is configured such that only an end portion to which the radiation emitting unit 14 is attached can be rotated with the imaging table 13 fixed.

A radiation detector 15, such as a flat panel detector, is provided in the imaging table 13. The radiation detector 15 has a radiation detection surface 15A. In addition, for example, a circuit substrate, which is provided with a charge amplifier that converts a charge signal read from the radiation detector 15 into a voltage signal, a correlated double sampling circuit that samples the voltage signal output from the charge amplifier, an analog-digital (AD) conversion unit that converts the voltage signal into a digital signal, and the like, is provided in the imaging table 13.

A radiation source 16 is accommodated in the radiation emitting unit 14. The radiation source 16 emits radiation such as γ-rays or X-rays. The time when the radiation source 16 emits the radiation and radiation generation conditions in the radiation source 16, that is, the selection of materials of a target and a filter, a tube voltage, an irradiation time, and the like are controlled by the console 2.

Further, the arm portion 12 is provided with a compression plate 17 that is disposed above the imaging table 13 and presses and compresses the breast M, a support portion 18 that supports the compression plate 17, and a movement mechanism 19 that moves the support portion 18 in an up-down direction in FIGS. 1 and 2. In addition, an interval between the compression plate 17 and the imaging table 13, that is, a compression thickness is input to the console 2.

The console 2 has a function of controlling the mammography apparatus 1 using an imaging order and various types of information acquired from a radiology information system (RIS) (not illustrated) or the like through a wireless communication local area network (LAN) or the like and instructions or the like directly given by a technician or the like. Specifically, the console 2 directs the mammography apparatus 1 to perform the tomosynthesis imaging on the breast M, acquires a plurality of projection images as described below, and reconstructs the plurality of projection images to generate a plurality of tomographic images. For example, in this embodiment, a server computer is used as the console 2.

The image storage system 3 is a system that stores image data such as radiographic images, projection images, and tomographic images captured by the mammography apparatus 1. The image storage system 3 extracts an image corresponding to a request from, for example, the console 2 and the image processing device 4 from the stored images and transmits the image to a device that is the source of the request. A specific example of the image storage system 3 is a picture archiving and communication system (PACS).

Figure 3:
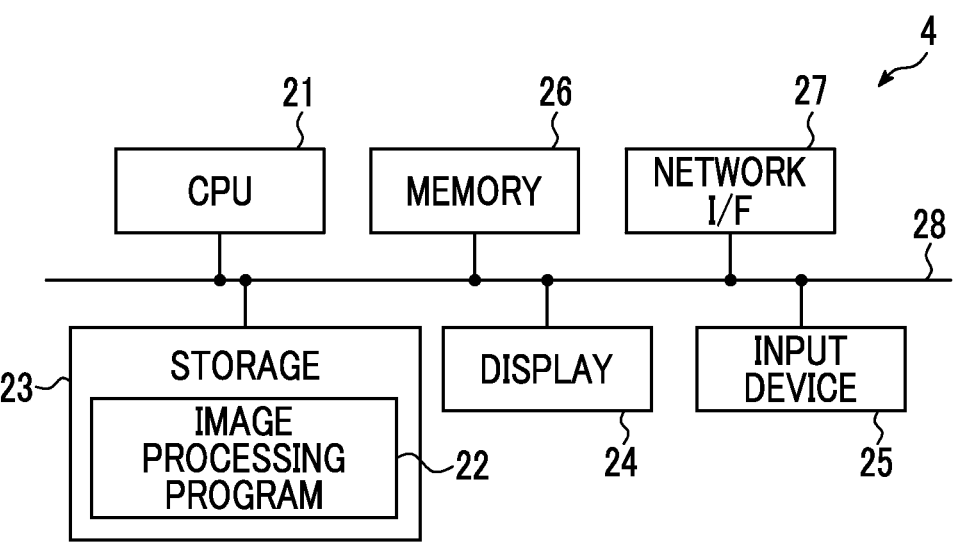
FIG. 3 is a block diagram illustrating an example of a hardware configuration of the image processing device.

Next, the image processing device 4 according to a first embodiment will be described. First, a hardware configuration of the image processing device 4 according to the first embodiment will be described with reference to FIG. 3. As illustrated in FIG. 3, the image processing device 4 is a computer, such as a workstation, a server computer, or a personal computer, and comprises a central processing unit (CPU) 21, a non-volatile storage 23, and a memory 26 as a temporary storage area. In addition, the image processing device 4 comprises a display 24, such as a liquid crystal display, an input device 25, such as a keyboard and a mouse, and a network interface (I/F) 27 that is connected to a network (not illustrated). The CPU 21, the storage 23, the display 24, the input device 25, the memory 26, and the network I/F 27 are connected to a bus 28. The CPU 21 is an example of a "processor" according to the technology of the present disclosure. In addition, the memory 26 is an example of a "memory" according to the technology of the present disclosure. Furthermore, the memory 26 may be provided in the CPU 21.

The storage 23 is implemented by a hard disk drive (HDD), a solid state drive (SSD), a flash memory, or the like. An image processing program 22 installed in the image processing device 4 is stored in the storage 23 as a storage medium. The CPU 21 reads the image processing program 22 from the storage 23, expands the image processing program 22 in the memory 26, and executes the expanded image processing program 22. The image processing program 22 is an example of a "program for operating an image processing device" according to the technology of the present disclosure.

In addition, the image processing program 22 is stored in a storage device of a server computer connected to the network or a network storage in a state in which it can be accessed from the outside and is downloaded and installed in the computer constituting the image processing device 4 as required. Alternatively, the image processing program 22 is recorded on a recording medium, such as a digital versatile disc (DVD) or a compact disc read only memory (CD-ROM), is distributed, and is installed in the computer constituting the image processing device 4 from the recording medium.

Figure 4:
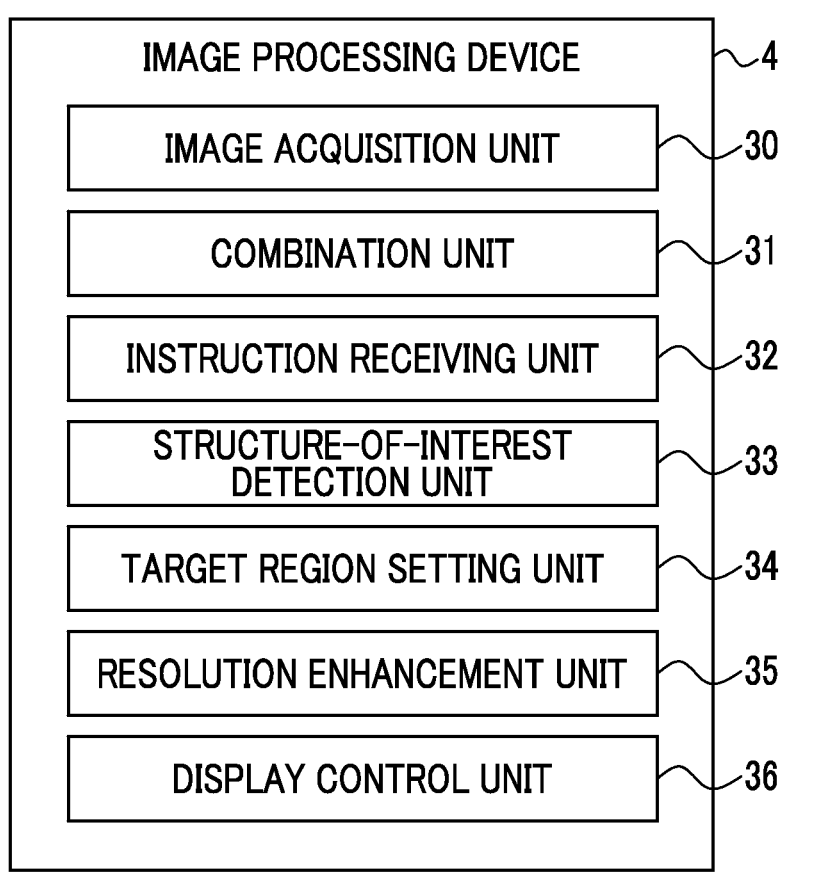
FIG. 4 is a diagram illustrating a functional configuration of the image processing device.

Next, a functional configuration of the image processing device 4 according to the first embodiment will be described. FIG. 4 is a diagram illustrating the functional configuration of the image processing device 4 according to the first embodiment. As illustrated in FIG. 4, the image processing device 4 comprises an image acquisition unit 30, a combination unit 31, an instruction receiving unit 32, a structure-of-interest detection unit 33, a target region setting unit 34, a resolution enhancement unit 35, and a display control unit 36. The CPU 21 executes the image processing program 22 such that the image processing device 4 functions as the image acquisition unit 30, the combination unit 31, the instruction receiving unit 32, the structure-of-interest detection unit 33, the target region setting unit 34, the resolution enhancement unit 35, and the display control unit 36.

The image acquisition unit 30 acquires the tomographic image from the console 2 or the image storage system 3 through the network I/F 27. In addition, the image acquisition unit 30 may acquire the projection image from the console 2 or the image storage system 3 through the network I/F 27.

Here, tomosynthesis imaging for generating tomographic images will be described with reference to FIG. 5. The console 2 controls the mammography apparatus 1 such that the mammography apparatus 1 performs the tomosynthesis imaging. In the tomosynthesis imaging, the mammography apparatus 1 rotates the arm portion 12 (see FIG. 1) about the rotation shaft 11 to move the radiation source 16 to each of radiation source positions S1, S2, . . . , Sn. The angle at which the breast M is irradiated with the radiation is changed by this movement of the radiation source 16 to each radiation source position. Further, the breast M, which is the object, is irradiated with the radiation under predetermined imaging conditions for tomosynthesis imaging at a plurality of radiation source positions on a movement trajectory of the radiation source 16. The radiation transmitted through the breast M is detected by the radiation detector 15, and the radiation detector 15 outputs projection images Gi (i=1 to n, n is the number of radiation source positions and is, for example, 15) based on the detected radiation to the console 2. Then, the console 2 acquires a plurality of projection images G1, G2, . . . , Gn corresponding to the plurality of radiation source positions S1 to Sn, respectively. In addition, for example, the same dose of radiation is emitted to the breast M at each of the radiation source positions S1 to Sn.

Figure 5:
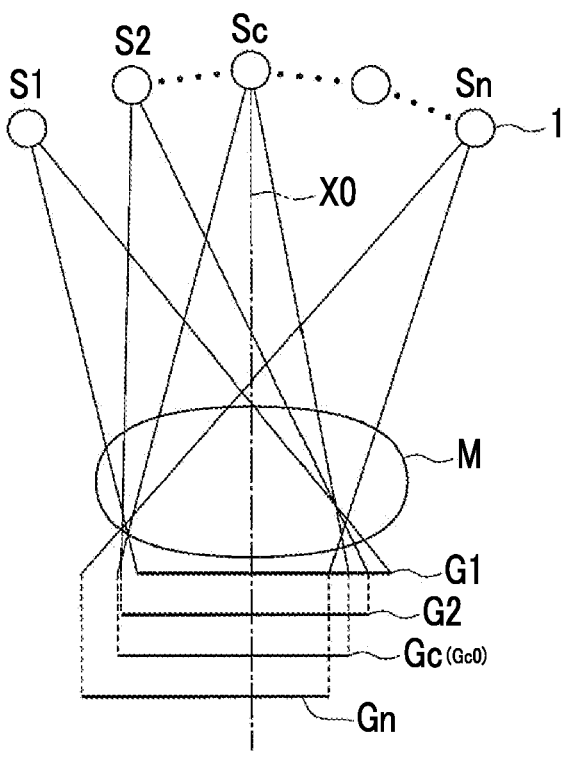
FIG. 5 is a diagram illustrating acquisition of projection images.

Further, in FIG. 5, a radiation source position Sc is a radiation source position where an optical axis X0 of the radiation emitted from the radiation source 16 is orthogonal to the detection surface 15A of the radiation detector 15. That is, the radiation source position Sc is a position for simple imaging in which the radiation source 16 faces the radiation detector 15 and emits radiation. In this embodiment, at the radiation source position Sc, the breast M may be irradiated with a higher dose of radiation than that at other radiation source positions to acquire a simple two-dimensional image Gc0. The simple two-dimensional image Gc0 is an example of a "two-dimensional image" according to the technology of the present disclosure.

Figure 6:
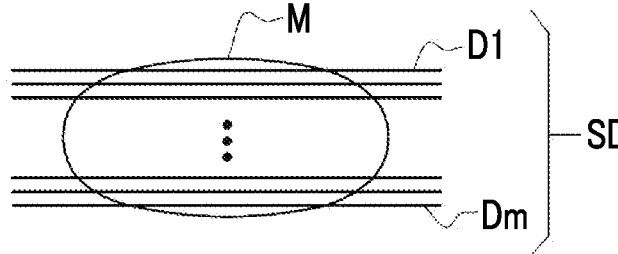
FIG. 6 is a diagram illustrating a tomographic image group.

The console 2 reconstructs the plurality of projection images Gi acquired by the tomosynthesis imaging to generate tomographic images in which the desired tomographic planes of the breast M have been highlighted. Specifically, the console 2 reconstructs a plurality of tomographic images Dj (j=1 to m, m is the number of tomographic images and is, for example 50) in each of a plurality of tomographic planes of the breast M as illustrated in FIG. 6 from the plurality of projection images Gi, using a known back projection method, such as a simple back projection method or a filtered back projection method. During the reconstruction, a pixel having three-dimensional coordinates in a three-dimensional space including the breast M is set, the pixel values of the corresponding pixels in the plurality of projection images Gi are back-projected, and the pixel value of the set three-dimensional pixel is calculated. The plurality of tomographic images Dj constitute a tomographic image group SD which is three-dimensional volume data in the set three-dimensional space. In addition, in the first embodiment, it is assumed that the pixel values of the tomographic images Dj are larger as brightness is higher (that is, closer to white) and are smaller as the brightness is lower (that is, closer to black).

In the tomographic image group SD, the plurality of tomographic images Dj are arranged along a depth direction of the tomographic planes in the breast M. In the plurality of tomographic images Dj, the coordinate positions of each pixel in each tomographic plane correspond to each other. Here, in the plurality of tomographic images Dj, pixels at the same coordinate position in the tomographic planes are referred to as corresponding pixels. In addition, the tomographic images Dj have a first resolution. The first resolution is determined according to the resolution of the projection images Gi output by the radiation detector 15 and the number of coordinate positions in the tomographic planes in the three-dimensional space set in a case in which the tomographic image group SD is reconstructed from the projection images Gi by the back projection method or the like.

The console 2 transmits the generated tomographic image group SD to the image processing device 4 or the image storage system 3.

Figure 7:
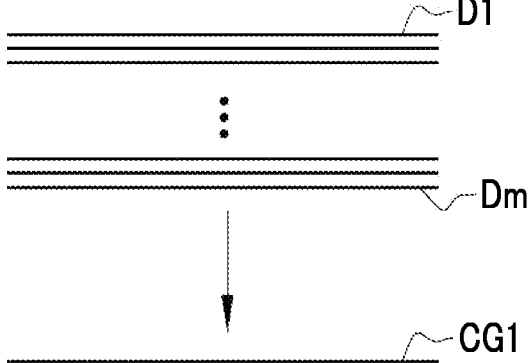
FIG. 7 is a diagram illustrating the generation of a composite two-dimensional image.

The combination unit 31 combines the plurality of tomographic images Dj in the tomographic image group SD to generate a composite two-dimensional image CG1. FIG. 7 is a diagram illustrating a method for generating the composite two-dimensional image CG1. As illustrated in FIG. 7, the combination unit 31 combines the corresponding pixels of the plurality of tomographic images Dj in the depth direction in which the tomographic planes of the tomographic images Dj are arranged (that is, the depth direction of the breast M) to generate the composite two-dimensional image CG1. As a combination method, a well-known composite image generation technique, such as an addition method, an averaging method, a maximum intensity proj ection method, or a minimum intensity projection method for the pixel values of the corresponding pixels in the plurality of tomographic images Dj, can be used. Here, since the tomographic images Dj have the first resolution, the composite two-dimensional image CG1 also has the first resolution. The composite two-dimensional image CG1 is an example of the "two-dimensional image" according to the technology of the present disclosure, similarly to the simple two-dimensional image Gc0.

In the combination of each pixel of the composite two-dimensional image CG1, for the tomographic images Dj used for the combination, for example, the corresponding pixels of the tomographic images Dj of all of the tomographic planes may be used to calculate the average value of the pixel values of these pixels or the like. Not the corresponding pixels of all of the tomographic images Dj but the corresponding pixels of some of the tomographic images Dj may be used, and the average value of the pixel values of some pixels or the like may be used.

For example, only the pixels of three tomographic images D1, D2, and D3 of three tomographic planes selected from all of the tomographic images Dj may be used, and the average value of the pixel values may be used as the pixel value. In addition, the tomographic planes used for calculating the pixel values may be changed for each pixel of the composite two-dimensional image CG1. For example, for a certain pixel, only the pixels of three tomographic images D1, D2, and D3 of three tomographic planes are used, and the average value of the pixel values or the like is used as the pixel value. For other pixels, only the pixels of two tomographic images D2 and D3 of two tomographic planes are used, and the average value of the pixel values or the like is used as the pixel value.

Figure 8:
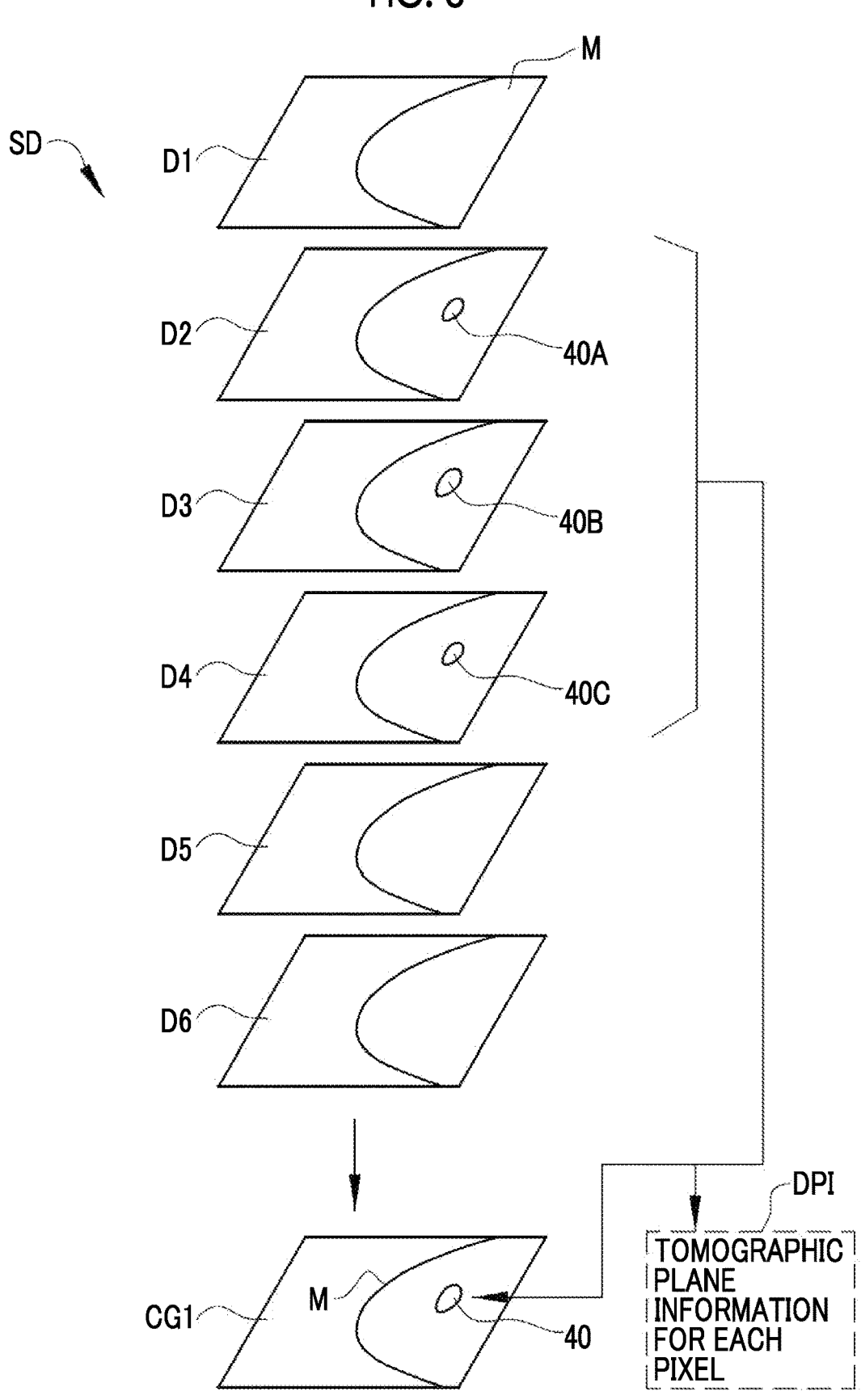
FIG. 8 is a diagram illustrating in detail the generation of the composite two-dimensional image.

As illustrated in FIG. 8, for a portion in which a structure of interest 40 is present in the tomographic image group SD, the combination unit 31 selects some tomographic images Dj in which the structure of interest 40 is present from the plurality of tomographic images Dj. Then, the combination unit 31 performs combination using only the pixels of the selected tomographic images Dj. In FIG. 8, structures of interest 40A, 40B, and 40C are present only in the tomographic images D2 to D4 of three tomographic planes among a plurality of tomographic images D1 to D6. In this case, the combination unit 31 combines pixels at the coordinate positions where the structure of interest 40 is present among the pixels of the composite two-dimensional image CG1, using only the pixels in which the structures of interest 40A to 40C corresponding to the structure of interest 40 are present in the three tomographic images D2 to D4. Similarly, for a portion of the breast M in which the structure of interest 40 is not present, combination is performed using the pixels of the plurality of tomographic images Dj. In addition, for a blank portion other than the breast M, for example, combination is performed using the pixels of all of the tomographic images Dj.

Further, the combination unit 31 records tomographic plane information DPI for each pixel which indicates the tomographic images Dj of the tomographic planes used for each pixel of the breast M in the composite two-dimensional image CG1 in association with the generated composite two-dimensional image CG1.

The instruction receiving unit 32 receives various instructions input by a user, such as a radiologist, through the input device 25. For example, the instruction receiving unit 32 receives an operation instruction related to the interpretation of the composite two-dimensional image CG1 and the tomographic images Dj from the user. In this embodiment, the operation instruction related to the interpretation is an instruction to input a designated region SR (see FIG. 10) in the composite two-dimensional image CG1. In a case in which the instruction receiving unit 32 receives the input instruction, the instruction receiving unit 32 outputs image information of the designated region SR to the structure-of-interest detection unit 33.

Figure 9:
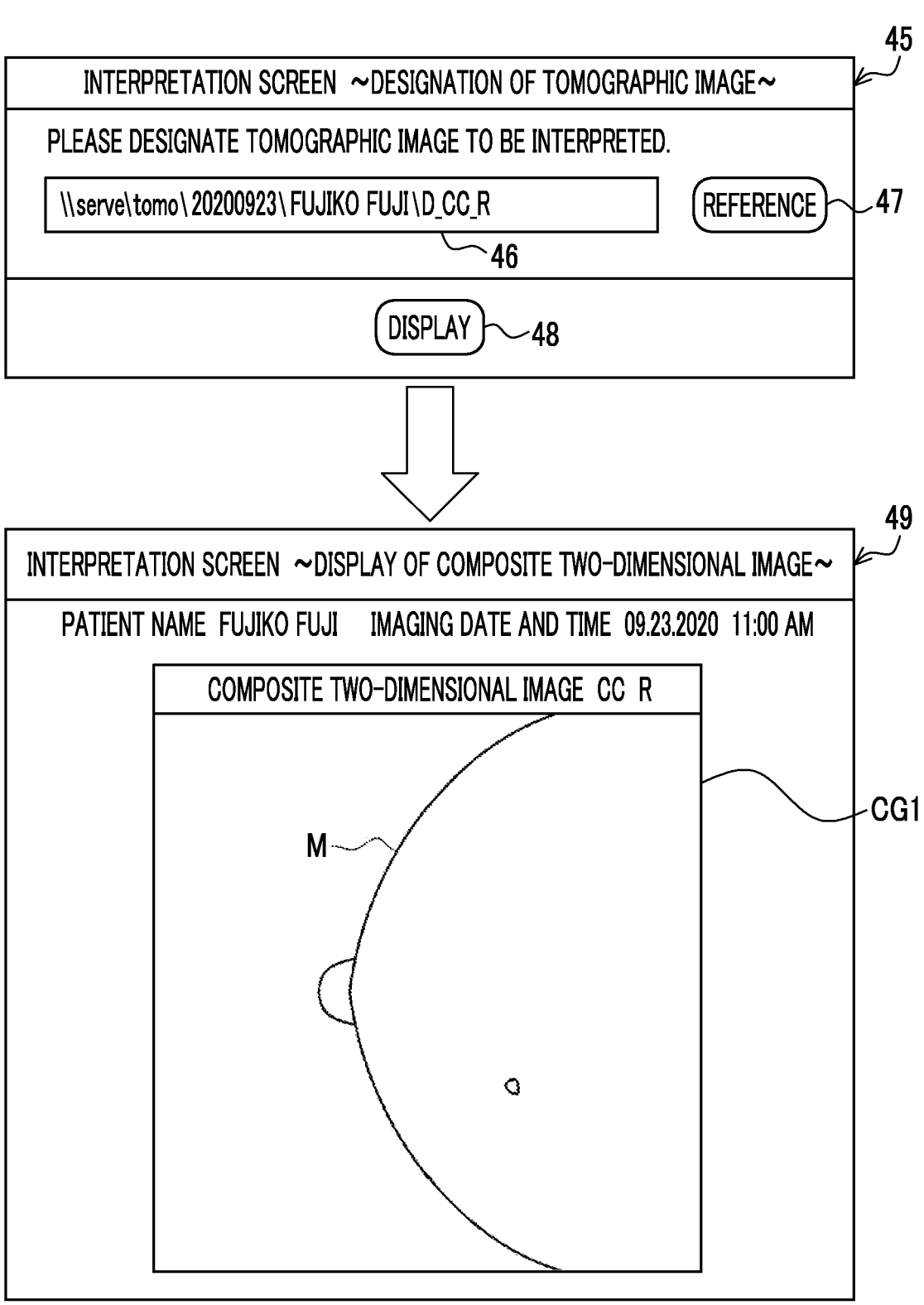
FIG. 9 is a diagram illustrating a screen for designating a tomographic image group and a screen including a composite two-dimensional image.

As illustrated in FIG. 9, the display control unit 36 displays a screen 45 for designating the tomographic image group SD received from the console 2 or the image storage system 3 on the display 24. The screen 45 is provided with an input box 46 for a file path of the tomographic image group SD, a reference button 47 for displaying Internet Explorer, and a display button 48. In a case in which the file path of a desired tomographic image group SD is input to the input box 46 and the display button 48 is selected, the image acquisition unit 30 transmits a request to distribute the tomographic image group SD whose file path has been input to the input box 46 to the console 2 or the image storage system 3. Then, the image acquisition unit 30 acquires the tomographic image group SD distributed from the console 2 or the image storage system 3 in response to the distribution request. The combination unit 31 generates the composite two-dimensional image CG1 from the tomographic image group SD. The display control unit 36 switches the display from the screen 45 to a screen 49 including the composite two-dimensional image CG1. That is, the operation of the display button 48 is an example of a "first display instruction for a two-dimensional image" according to the technology of the present disclosure.

Figure 10:
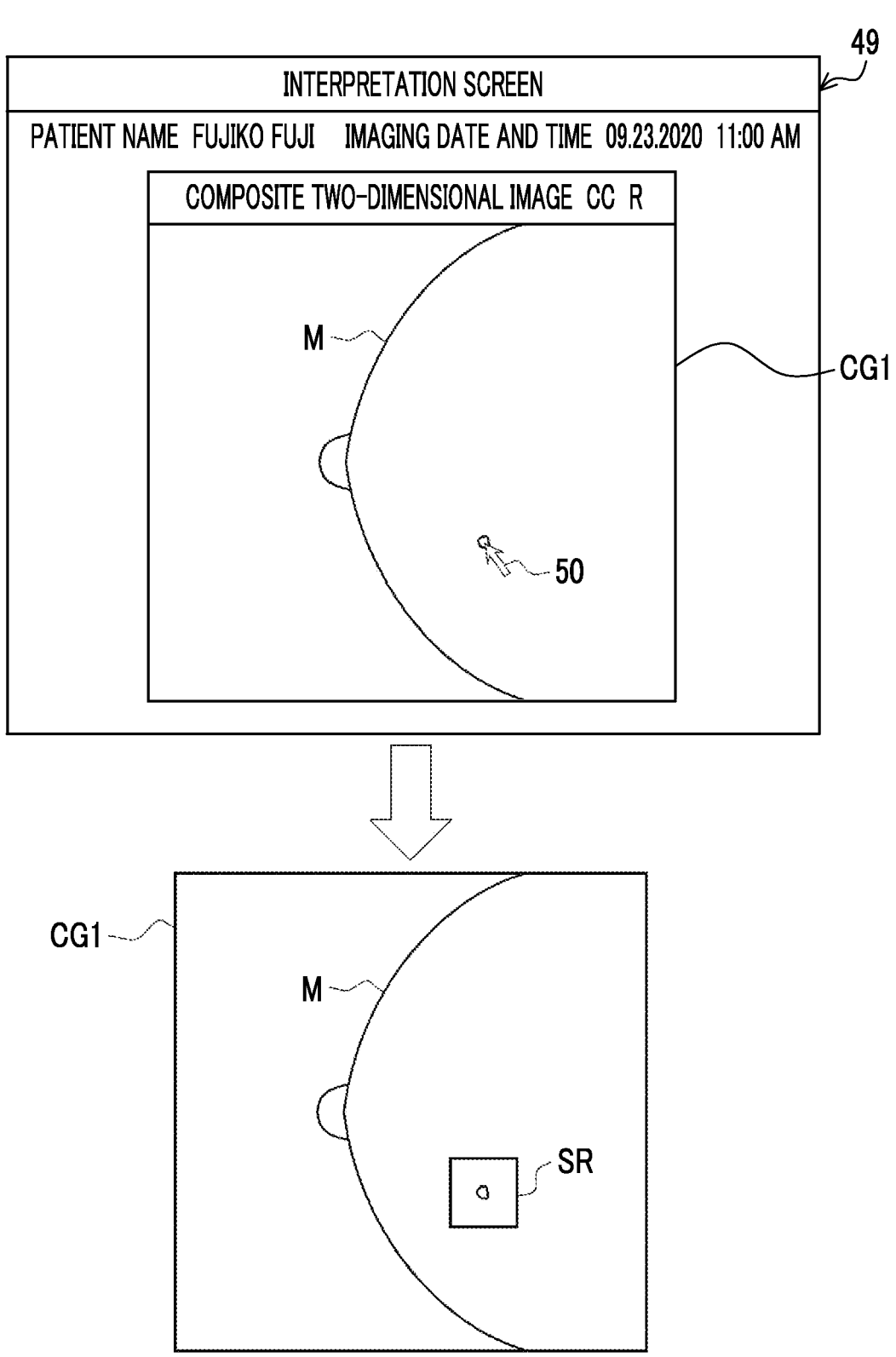
FIG. 10 is a diagram illustrating an aspect in which a designated region is set.

As illustrated in FIG. 10, the user places a cursor 50 of a mouse on a portion of interest of the breast M in the composite two-dimensional image CG1 on the screen 49 and clicks the portion of interest. Then, the designated region SR including the clicked point is set on the composite two-dimensional image CG1. That is, the operation of placing the cursor 50 of the mouse on the portion of interest of the breast M and clicking the portion of interest is an example of an "instruction to input a designated region" according to the technology of the present disclosure. At the same time, the operation of placing the cursor 50 of the mouse on the portion of interest of the breast M and clicking the portion of interest is also an example of a "second display instruction for a high-resolution partial image" according to the technology of the present disclosure. In addition, the simple two-dimensional image Gc0 may be displayed instead of the composite two-dimensional image CG1, and an instruction to input the designated region SR in the simple two-dimensional image Gc0 may be received.

The designated region SR is a square shape that has the clicked point as its center and has a size of, for example, 500 pixels×500 pixels. Further, the shape of the designated region SR is not limited to a rectangular shape and may be any shape such as a circular shape. In addition, the size of the designated region SR may be changed according to the size of the structure of interest 40 detected by the structure-of-interest detection unit 33. Similarly, the size of the designated region SR may be changed according to the type of the structure of interest 40 detected by the structure-of-interest detection unit 33. For example, in a case in which the structure of interest 40 is a tumor 51 (see FIG. 11), the size of the designated region SR is 500 pixels×500 pixels. In a case in which the structure of interest 40 is a calcification 53 (see FIG. 11), the size of the designated region SR is 50 pixels×50 pixels. Alternatively, a region surrounded by the contour of the structure of interest 40 detected by the structure-of-interest detection unit 33 may be set as the designated region SR. Furthermore, a region that is surrounded freehand by the user and has any shape and size may be set as the designated region SR.

Figure 11:
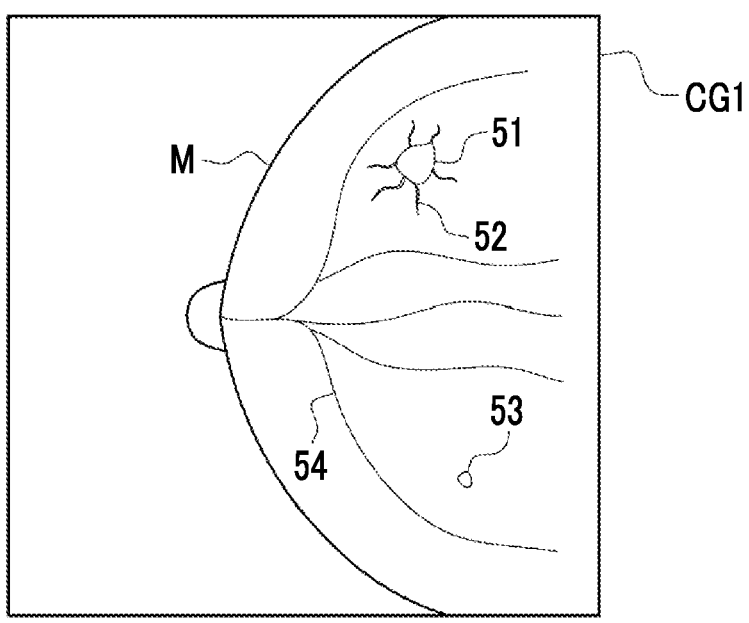
FIG. 11 is a diagram illustrating an example of a structure of interest.

The structure-of-interest detection unit 33 performs a process of detecting the structure of interest 40 in the designated region SR. Specifically, as illustrated in FIG. 11, the structure-of-interest detection unit 33 detects the tumor 51, a spicula 52, the calcification 53, and a linear structure 54 included in the breast M as the structures of interest 40. The linear structure is a mammary gland such as a lobule or a mammary duct. In a case in which the structure of interest 40 is detected from the designated region SR, the structure-of-interest detection unit 33 outputs information on the structure of interest 40, such as the coordinates of the pixels of the detected structure of interest 40, to the target region setting unit 34. On the other hand, in a case in which the structure of interest 40 is not detected from the designated region SR, the structure-of-interest detection unit 33 outputs the fact that the structure of interest 40 has not been detected to the target region setting unit 34. In addition, the structure-of-interest detection unit 33 may detect all of the tumor 51, the spicula 52, the calcification 53, and the linear structure 54 or may detect at least one of them.

The structure-of-interest detection unit 33 detects the structure of interest 40 from the designated region SR using a known computer-aided diagnosis (CAD) algorithm. In the CAD algorithm, the probability (likelihood) that the pixel in the designated region SR will be the structure of interest 40 is derived, and a pixel having a probability equal to or greater than a predetermined threshold value is detected as the structure of interest 40. In addition, the CAD algorithm is prepared for each type of structure of interest 40. In this embodiment, a CAD algorithm for detecting the tumor 51, a CAD algorithm for detecting the spicula 52, a CAD algorithm for detecting the calcification 53, and a CAD algorithm for detecting the linear structure 54 are prepared.

In addition, a technique for detecting the structure of interest 40 is not limited to the technique using the CAD. The structure of interest 40 may be detected from the designated region SR by a filtering process using a filter for detecting the structure of interest 40, a detection model which has been subjected to machine learning by deep learning and the like to detect the structure of interest 40, and the like as techniques other than the CAD.

Figure 12:
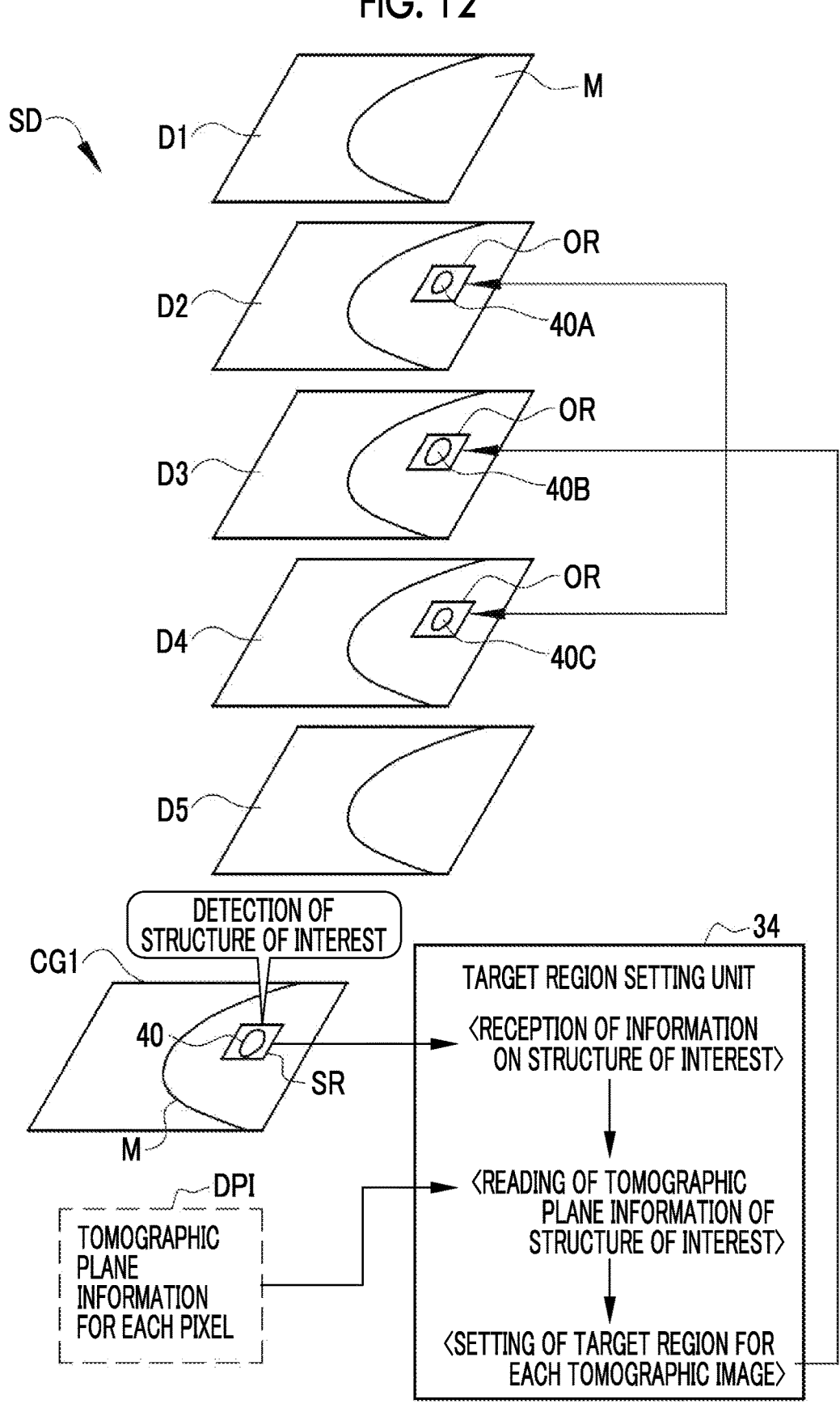
FIG. 12 is a diagram illustrating a process of a target region setting unit in a case in which the structure of interest is detected from the designated region.
Figure 13:
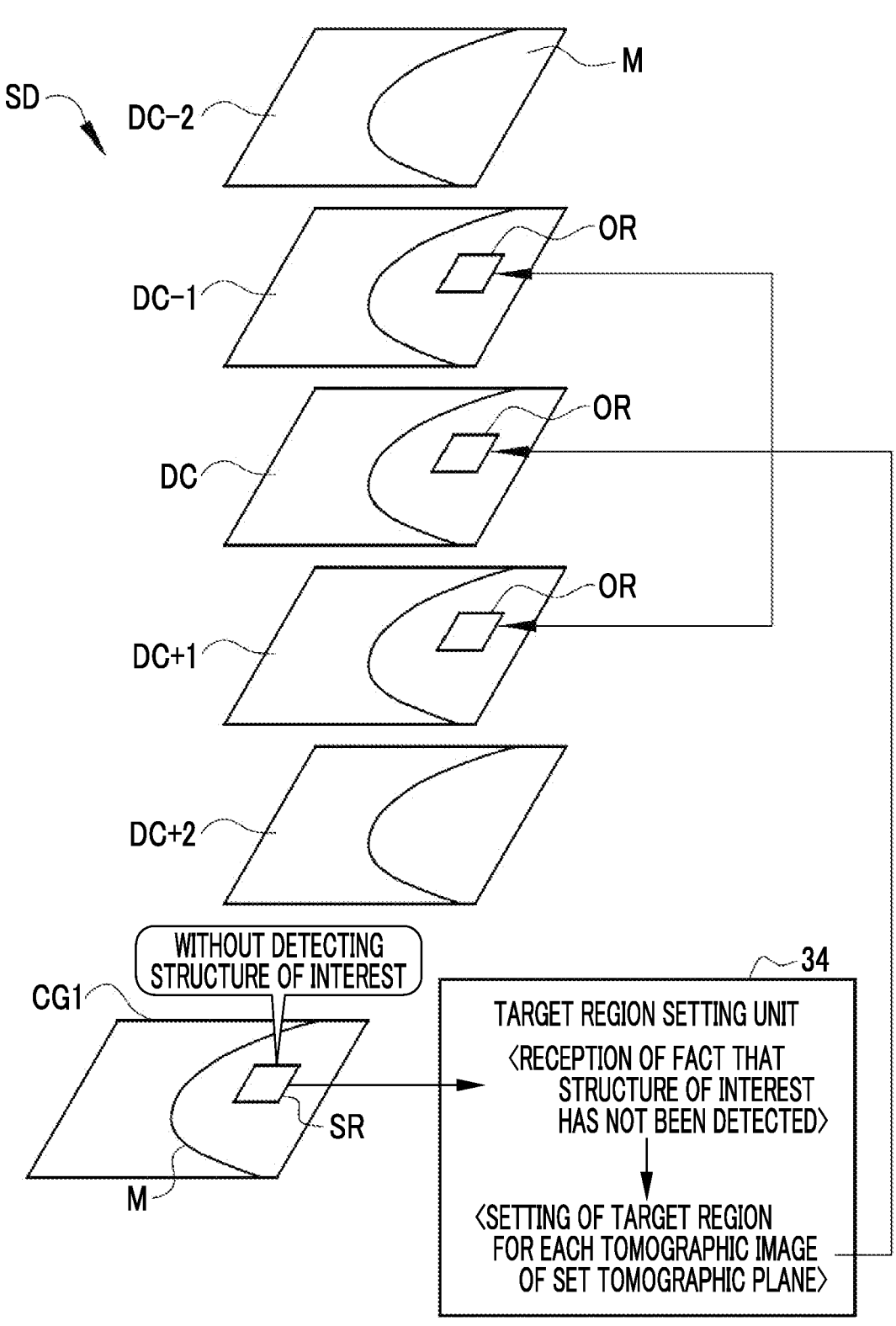
FIG. 13 is a diagram illustrating a process of the target region setting unit in a case in which the structure of interest is not detected from the designated region.

As illustrated in FIGS. 12 and 13, the target region setting unit 34 sets a partial region of the tomographic images Dj as the target region OR. The target region OR is a region that is to be subjected to a process of converting the resolution to a second resolution higher than the first resolution, that is, a resolution enhancement process and is a region including one or more pixels in each of the tomographic images Dj.

FIG. 12 illustrates a case in which the structure-of-interest detection unit 33 detects the structure of interest 40 from the designated region SR. In this case, the target region setting unit 34 sets a region including the structure of interest 40 in the tomographic images Dj as the target region OR. Specifically, the target region setting unit 34 receives the information of the structure of interest 40 from the structure-ofinterest detection unit 33. Then, the tomographic plane information DPI of the pixel of the structure of interest 40 indicated by the information of the structure of interest 40 is read. The target region setting unit 34 sets, as the target region OR, the same region as the designated region SR of the tomographic image Dj of the tomographic plane indicated by the read tomographic plane information DPI. FIG. 12 illustrates a case in which the target region OR is set in three tomographic images D2 to D4 of three tomographic planes in which the structures of interest 40A to 40C corresponding to the structure of interest 40 in the composite two-dimensional image CG1 are present. In addition, instead of the same region as the designated region SR, a region surrounded by the contour of the structure of interest 40 may be set as the target region OR.

On the other hand, FIG. 13 illustrates a case in which the structure-of-interest detection unit 33 does not detect the structure of interest 40 from the designated region SR. In this case, the target region setting unit 34 sets, as the target region OR, a region corresponding to the designated region SR in the tomographic image Dj of a predetermined set tomographic plane. Specifically, the target region setting unit 34 receives the fact that the structure of interest 40 has not been detected from the structure-of-interest detection unit 33. The target region setting unit 34 sets the same region as the designated region SR of the tomographic image Dj of the set tomographic plane as the target region OR. FIG. 13 illustrates a case in which the target region OR is set in a tomographic image DC of a central tomographic plane and tomographic images DC−1 and DC+1 of the tomographic planes above and below the tomographic image DC among a plurality of tomographic planes. That is, the tomographic images DC, DC−1, and DC+1 are examples of a "tomographic image of a set tomographic plane" according to the technology of the present disclosure. In this example, in the tomographic planes, the term "above" indicates the head side, and the "below" indicates the abdominal side.

The set tomographic planes are not limited to the central tomographic plane and the tomographic planes above and below the central tomographic plane given as an example. The set tomographic planes may be the central tomographic plane and d (d is an integer equal to or greater than 2) tomographic planes above and below the central tomographic plane. Further, the set tomographic planes may be the uppermost tomographic plane and d+1 tomographic planes below the uppermost tomographic plane, or may be the lowermost tomographic plane and d−1 tomographic planes above the lowermost tomographic plane. Furthermore, all of the tomographic planes may be set as the set tomographic planes.

In addition, the following can be considered as an example in which the structure-of-interest detection unit 33 does not detect the structure of interest 40 from the designated region SR. For example, in some cases, the user thinks that the structure of interest 40 is present in a region, places the cursor 50 on the region, and clicks the region. However, the structure of interest 40 is not actually present in the region. Alternatively, in some cases, the structure of interest 40 is not recognized in a region, but the user clicks the region to look at the region for checking.

Figure 14:
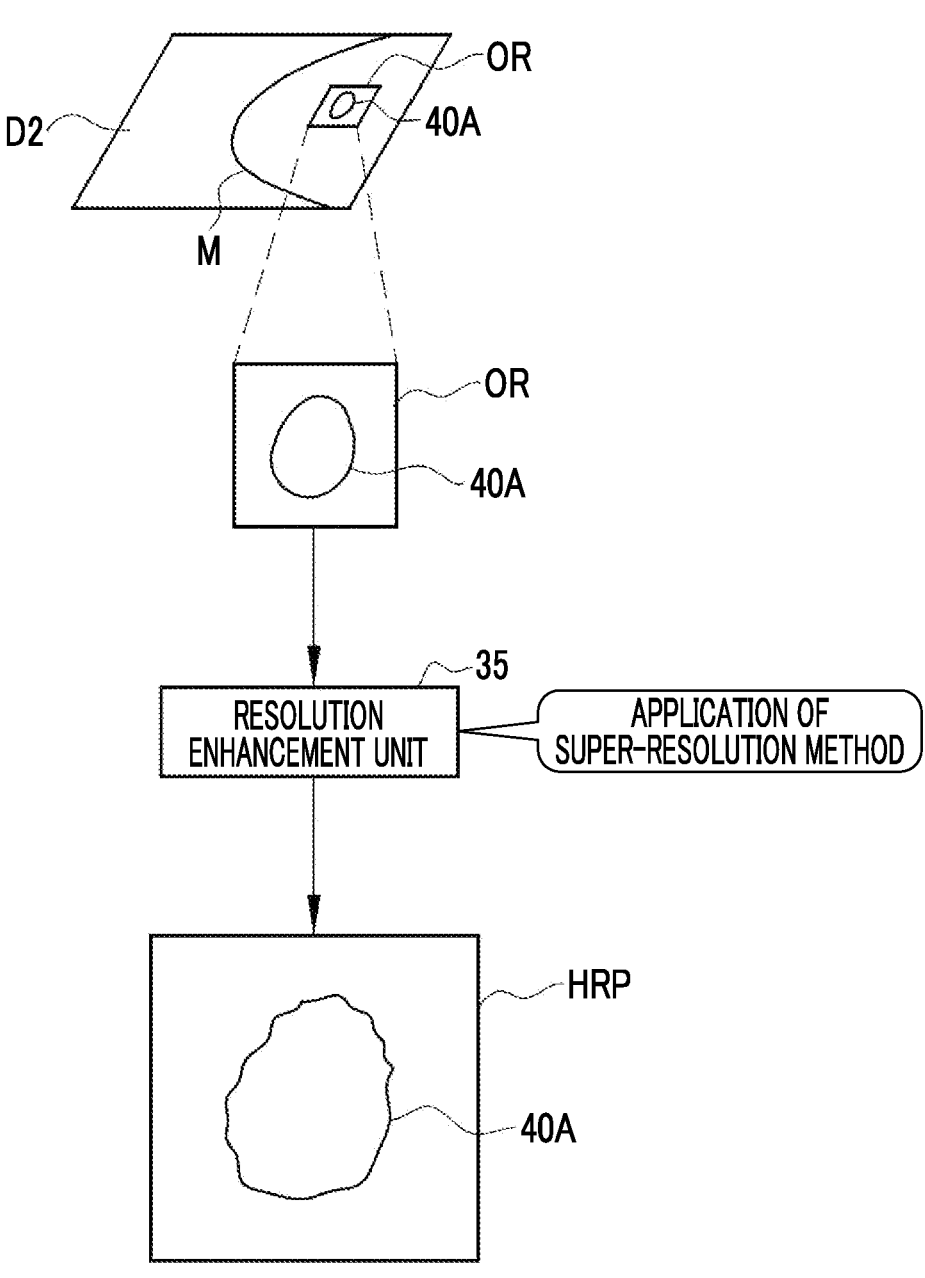
FIG. 14 is a diagram illustrating a process of a resolution enhancement unit.

As illustrated in FIG. 14, the resolution enhancement unit 35 performs a process of increasing the resolution of the target region OR from the first resolution to the second resolution. The second resolution is higher than the first resolution and indicates the number of pixels that is, for example, four times the number of pixels in the first resolution. The resolution enhancement unit 35 does not perform the resolution enhancement process on a region of the tomographic image Dj other than the target region OR. The resolution enhancement unit 35 performs the resolution enhancement process only on the target region OR in this way to generate the high-resolution partial image HRP of the target region OR. The high-resolution partial image HRP is an image in which the number of pixels is larger than that of the image of the original target region OR and details of, for example, the structure of interest 40 are expressed in high definition. The resolution enhancement unit 35 outputs the high-resolution partial image HRP to the display control unit 36.

FIG. 14 illustrates a case in which the resolution enhancement process is performed on the target region OR of the tomographic image D2 illustrated in FIG. 12. Further, in the case of FIG. 12, the resolution enhancement process is also performed on the target region OR in the tomographic images D3 and D4, which is not illustrated. Furthermore, in the case of FIG. 13, the resolution enhancement process is performed on each target region OR in the tomographic images DC, DC−1, and DC+1.

A super-resolution method is applied as the resolution enhancement process. The super-resolution method is a process of converting the resolution into a resolution that is higher than the resolution set in a case in which the tomographic images Dj are reconstructed on the basis of the projection images Gi. The method disclosed in JP2020-025786A can be given as an example of the super-resolution method. The super-resolution method disclosed in JP2020-025786A is a process using a trained model which has been subjected to machine learning to convert an input image into a super-resolution image. The trained model adds a new pixel between the pixels of the input image, interpolates the pixel value of the added new pixel, and outputs a super-resolution image. This trained model is constructed using, for example, any one of a convolutional neural network, a recurrent neural network, or a support vector machine.

In addition, the super-resolution method is not limited to the method disclosed in JP2020-025786A. For example, any high-order interpolation method, such as nearest neighbor interpolation, bilinear interpolation, and bicubic interpolation, can be used. Further, as described in <Daniel Glasner, et al. "Super-Resolution from a Single Image", ICCV, 29 Sep.-2 Oct. 2009>, a method can be used which extracts small regions (called patches) that repeatedly appear from an image and converts the original image into a super-resolution image using the pixel values of the extracted small regions.

In addition, the high-resolution partial image HRP may be generated using the tomographic images Dj which are adjacent to each other in the vertical direction. For example, for the target region OR set in the tomographic image D3 illustrated in FIG. 12, the target region OR set in the tomographic image D2 and the target region OR set in the tomographic image D4 are also used for increasing the resolution. In this case, the image of the target region OR in the tomographic images D2 to D4 is regarded as a three-dimensional image, and k-neighbor interpolation is performed using k pixels which are located closest to the pixels to be interpolated in the target region OR of the tomographic image D3. In addition, any value, such as 6 or 26, can be used as the value of k.

Figure 15:
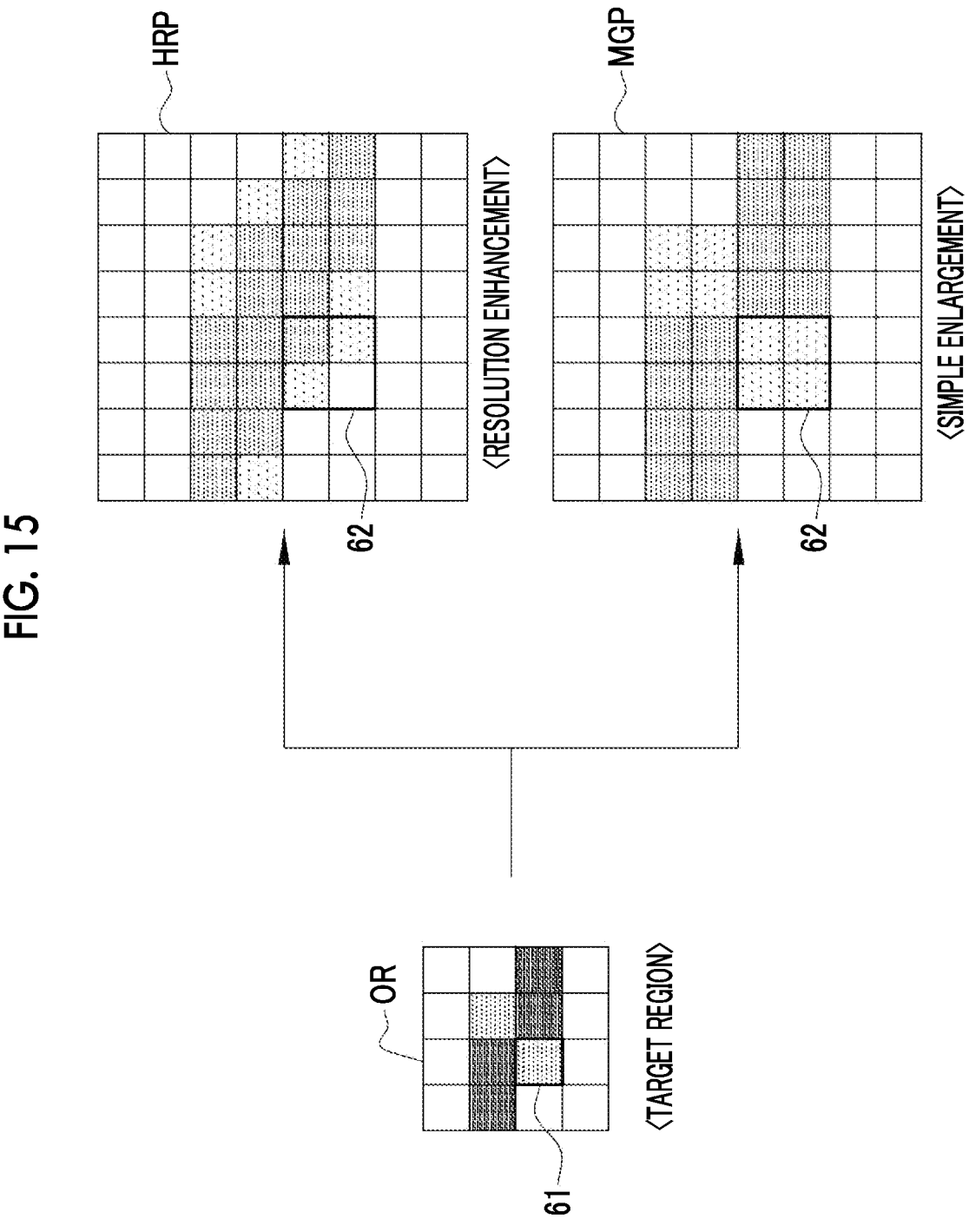
FIG. 15 is a diagram illustrating a difference between simple enlargement and resolution enhancement.

Here, the difference between simple enlargement and resolution enhancement will be described with reference to FIG. 15. FIG. 15 illustrates a case in which 4×4 pixels are converted into 8×8 pixels. In a case in which an image is enlarged in this way, one pixel is increased to 2×2 pixels. An image that has been simply enlarged (hereinafter, simply referred to as a simply enlarged image) MGP is an image in which the pixel value of the original pixel is simply assigned to the pixel values of the increased number of pixels. On the other hand, in the high-resolution partial image HRP, the pixel value of the original pixel is not simply assigned to the pixel values of the increased number of pixels, but the pixel values of the increased number of pixels are interpolated by the pixel values of the surrounding pixels to express the contour of the structure in higher definition. For example, a pixel 61 of the target region OR corresponds to a region 62 of 2×2 pixels in the simply enlarged image MGP and the high-resolution partial image HRP, and the pixels in the region 62 of the simply enlarged image MGP have the same pixel value as the pixel 61. On the other hand, the pixels in the region 62 of the high-resolution partial image HRP include a pixel having the same pixel value as the pixel 61 and a pixel having a pixel value different from that of the pixel 61.

Figure 16:
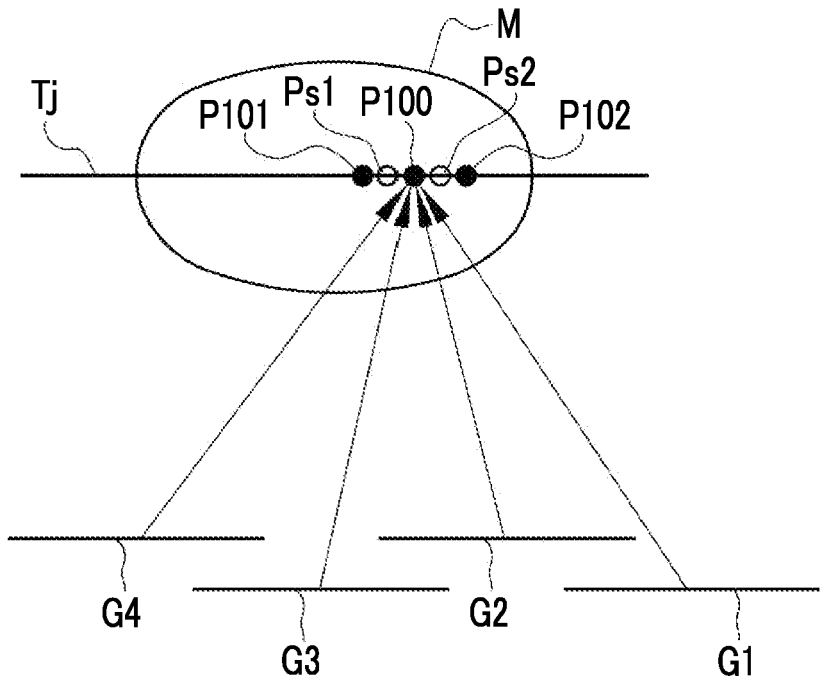
FIG. 16 is a diagram illustrating resolution enhancement using a back projection method.

Further, the resolution enhancement method includes a method using the proj ection images G1 used to reconstruct the tomographic image group SD as illustrated in FIG. 16, in addition to the super-resolution method that increases resolution on the basis of the tomographic images Dj. The method using the projection images Gi is a method that reconstructs the image of the target region OR selected in the tomographic images Dj as the high-resolution partial image HRP from the projection images Gi using a well-known back projection method such as a simple back projection method.

In the example illustrated in FIG. 16, back projection using four projection images G1 to G4 will be described. A pixel value at a coordinate position P100 on a certain tomographic plane Tj in the breast M is calculated by back-projecting the pixel values at the corresponding coordinate position in the projection images G1 to G4. The tomographic image Dj indicating the tomographic plane Tj is reconstructed by performing the back projection for each coordinate position in the tomographic plane Tj.

The resolution enhancement unit 35 further adds coordinate positions Ps1, Ps2, . . . between the coordinate positions P100 and P101, between the coordinate positions P101 and P102, . . . in the tomographic plane Tj set in a case in which the tomographic image Dj having the first resolution is reconstructed and back-projects the pixel values of the corresponding coordinate positions in the projection images G1 to G4 to the added coordinate positions Psi, Ps2, . . . . Therefore, pixel values are also calculated for the coordinate positions Ps1, Ps2, . . . added in the tomographic plane Tj. The resolution enhancement unit 35 uses the projection images Gi in this way to generate the high-resolution partial image HRP having the second resolution corresponding to the target region OR.

Figure 17:
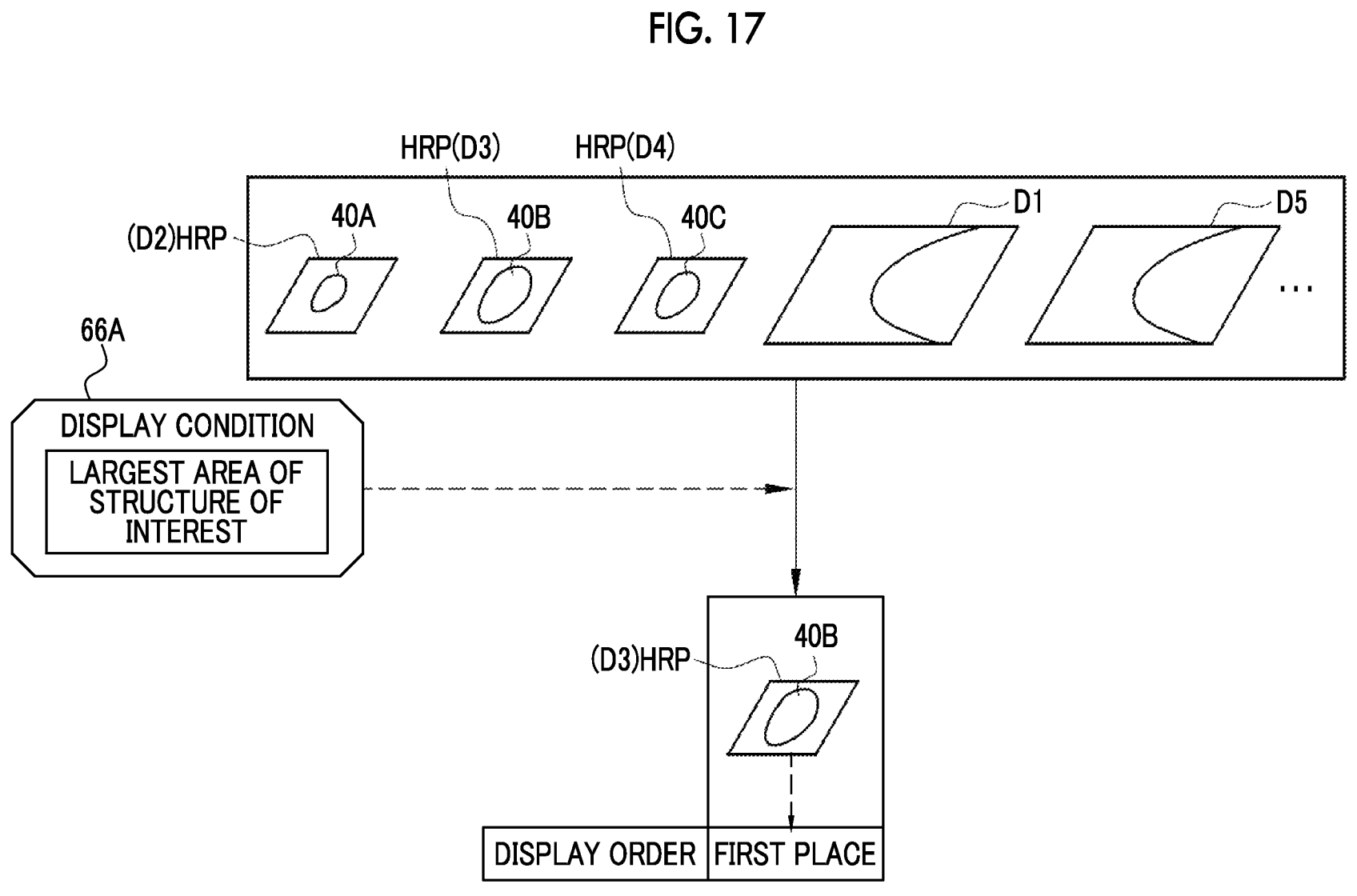
Figure 18:
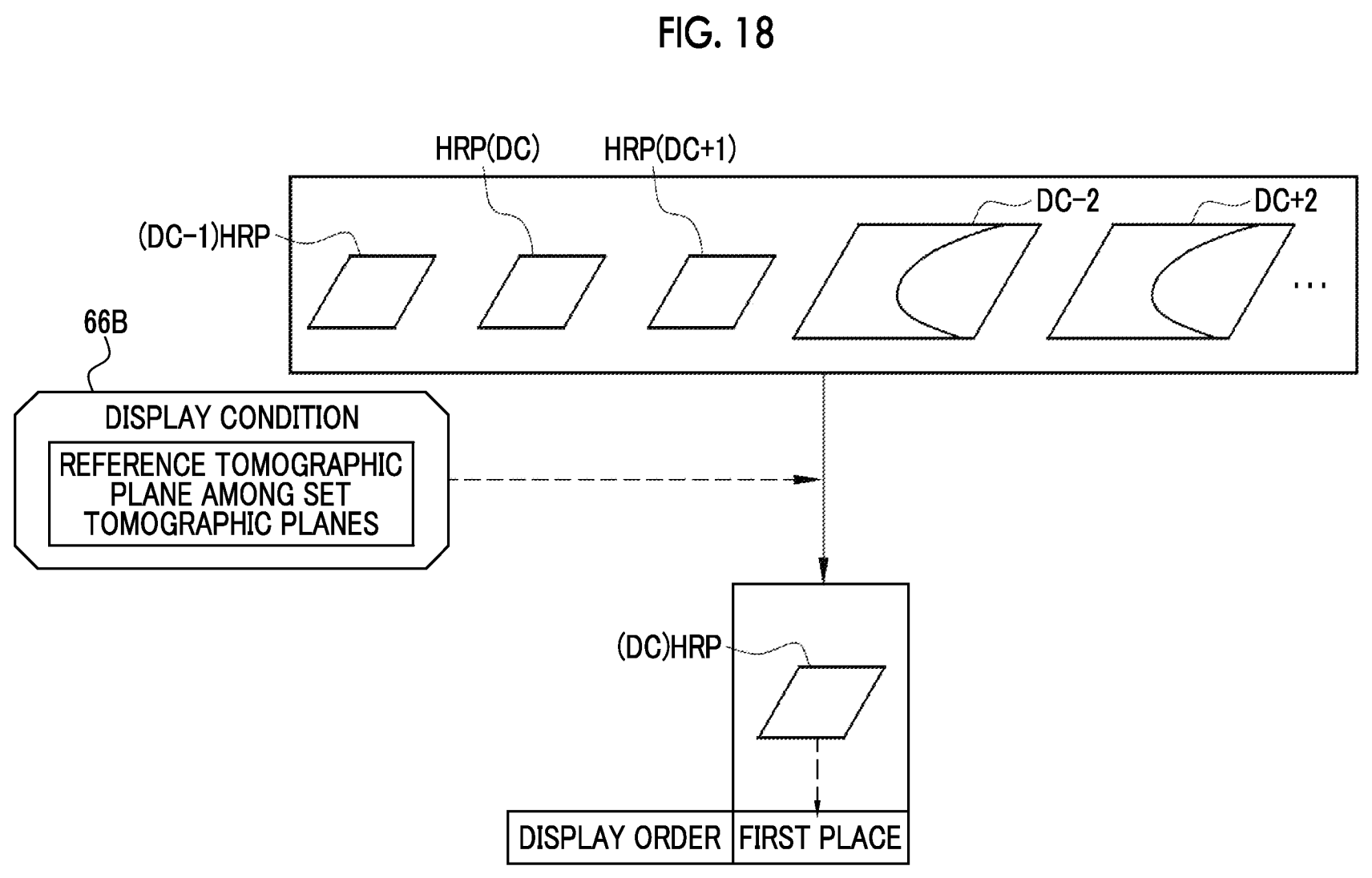

As illustrated in FIGS. 17 and 18, the display control unit 36 determines the display order of the high-resolution partial images HRP and the tomographic images Dj on the basis of a display condition 66A or 66B.

FIG. 17 illustrates a case in which the structure-of-interest detection unit 33 detects the structure of interest 40 from the designated region SR as in the case of FIG. 12. In this case, the display control unit 36 determines a display order on the basis of the display condition 66A. The content of the display condition 66A is the "largest area of the structure of interest". Therefore, the display control unit 36 determines that a high-resolution partial image HRP having the largest area of the captured structure of interest 40, that is, having the largest number of pixels of the captured structure of interest 40 among a plurality of high-resolution partial images HRP is displayed first. The display control unit 36 determines the display order of the high-resolution partial images HRP other than the high-resolution partial image HRP having the largest number of pixels of the captured structure of interest 40 in descending order of the area of the captured structure of interest 40. In addition, the display control unit 36 sets the display order of other tomographic images Dj, in which no target region OR is not set and which have not been used to generate the high-resolution partial images HRP, such that the tomographic images Dj rank lower than the high-resolution partial images HRP and the tomographic images Dj of the upper tomographic planes rank higher.

In FIG. 17, the structure of interest 40B included in the high-resolution partial image HRP(D3) generated from the tomographic image D3 has the largest area. The structure of interest 40C included in the high-resolution partial image HRP(D4) generated from the tomographic image D4 has the second largest area. The structure of interest 40A included in the high-resolution partial image HRP(D2) generated from the tomographic image D2 has the smallest area. Therefore, the display control unit 36 determines that the high-resolution partial image HRP(D3) is displayed first. For example, the subsequent high-resolution partial images HRP are displayed in descending order of the area of the structure of interest 40. Further, the display order of other tomographic images Dj that have not been used to generate the high-resolution partial images HRP is set such that the tomographic images Dj rank lower than the high-resolution partial images HRP and the tomographic images Dj of the upper tomographic planes rank higher. In addition, the content of the display condition 66A may be that the high-resolution partial image HRP in which the three-dimensional center of the structure of interest 40 is present is displayed first. Alternatively, the content of the display condition 66A may be that the high-resolution partial image HRP generated from the tomographic image Dj of the uppermost or lowermost tomographic plane among a plurality of tomographic images Dj having the same structure of interest 40 is displayed first.

On the other hand, FIG. 18 illustrates a case in which the structure-of-interest detection unit 33 does not detect the structure of interest 40 from the designated region SR as in the case of FIG. 13. In this case, the display control unit 36 determines the display order on the basis of the display condition 66B. The content of the display condition 66B is "a reference tomographic plane among the set tomographic planes". Therefore, the display control unit 36 determines that the high-resolution partial image HRP generated from the tomographic image Dj of the reference tomographic plane among the plurality of high-resolution partial images HRP is displayed first. The display control unit 36 sets the display order of the high-resolution partial images HRP other than the high-resolution partial image HRP generated from the tomographic image Dj of the reference tomographic plane such that the high-resolution partial image HRP generated from the tomographic image Dj of the upper tomographic plane ranks higher. Further, as in the case of FIG. 17, the display control unit 36 sets the display order of other tomographic images Dj, in which the target region OR is not set and which have not been used to generate the high-resolution partial images HRP, such that the tomographic images Dj rank lower than the high-resolution partial images HRP and the tomographic images Dj of the upper tomographic planes rank higher.

In FIG. 18, the display control unit 36 determines that the high-resolution partial image HRP(DC) generated from the tomographic image DC of the central tomographic plane, which is the reference tomographic plane, is displayed first. The display order of the subsequent high-resolution partial images HRP is set such that the high-resolution partial image for the upper tomographic plane ranks higher. In addition, the display order of other tomographic images Dj that have not been used to generate the high-resolution partial images HRP is set such that the tomographic images Dj rank lower than the high-resolution partial images HRP and the tomographic images Dj of the upper tomographic planes rank higher. In addition, the reference tomographic plane may be the uppermost tomographic plane or the lowermost tomographic plane.

Figure 19:
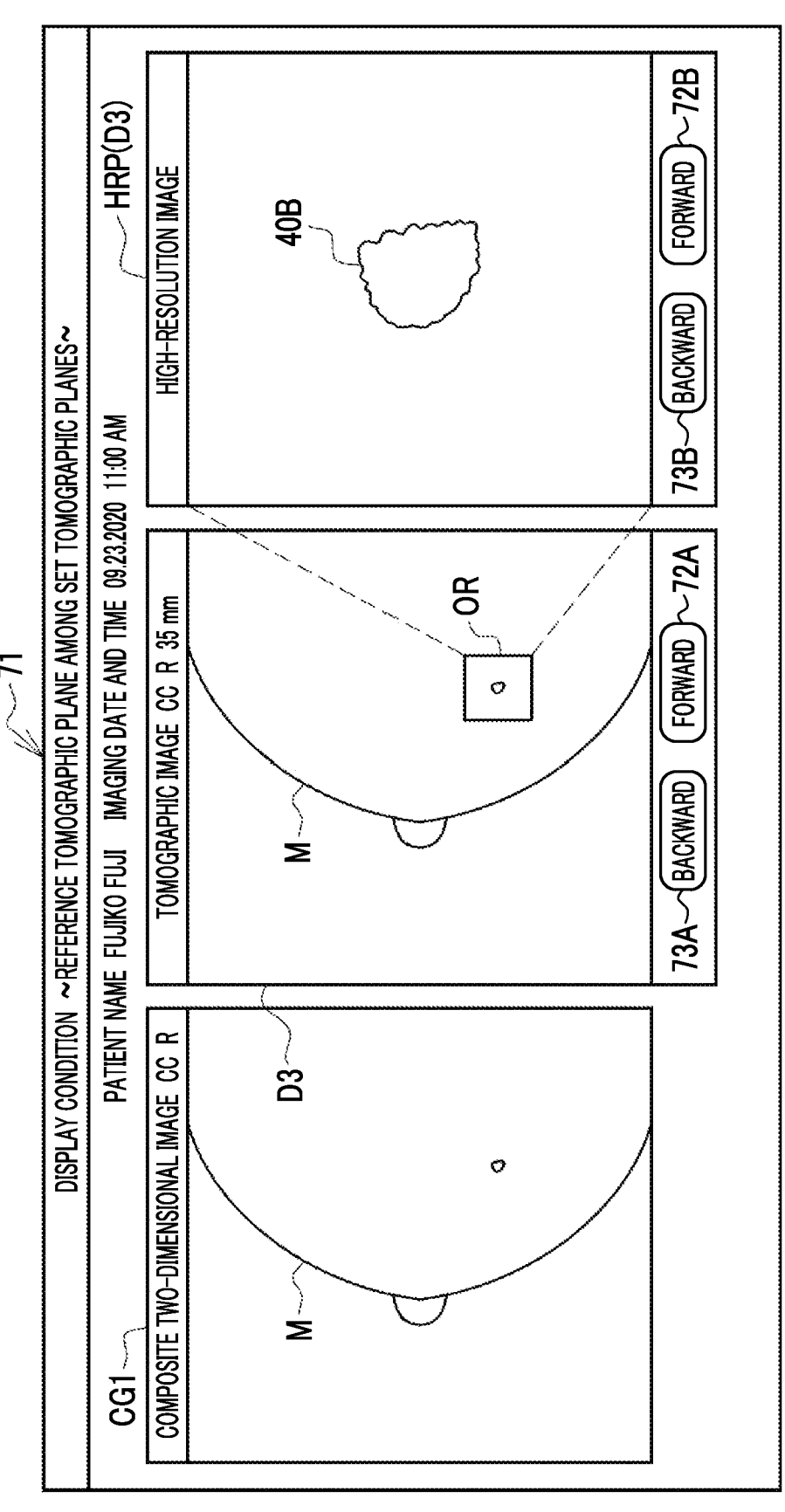
FIG. 19 is a diagram illustrating a screen including a composite two-dimensional image, a tomographic image, and a high-resolution partial image.

The display control unit 36 displays a screen 71 illustrated in FIG. 19 on the display 24 in a case in which the high-resolution partial image HRP determined to be displayed first is input from the resolution enhancement unit 35. The composite two-dimensional image CG1, the tomographic image Dj, and the high-resolution partial image HRP are displayed side by side on the screen 71. The target region OR is displayed in the tomographic image Dj in which the target region OR is designated to generate the high-resolution partial image HRP. A forward button 72A and a backward button 73A for sequentially displaying the tomographic images Dj of a plurality of tomographic planes one by one are provided below the tomographic image Dj. Further, a forward button 72B and a backward button 73B for sequentially displaying a plurality of high-resolution partial images HRP one by one are provided below the high-resolution partial image HRP. The instruction receiving unit 32 receives an instruction to switch the display of the tomographic image Dj input by the operation of the forward button 72A and the backward button 73A and an instruction to switch the display of the high-resolution partial image HRP input by the operation of the forward button 72B and the backward button 73B. The instruction to switch the display of the high-resolution partial image HRP input by the operation of the forward button 72B and the backward button 73B is an example of a "second display instruction for the high-resolution partial image" according to the technology of the present disclosure. FIG. 19 illustrates an example in which the tomographic image D3 and the high-resolution partial image HRP(D3) generated from the tomographic image D3 are displayed. In addition, the tomographic image Dj may not be displayed, and only the composite two-dimensional image CG1 and the high-resolution partial image HRP may be displayed. In this case, the target region OR is displayed on the composite two-dimensional image CG1.

Figure 20:
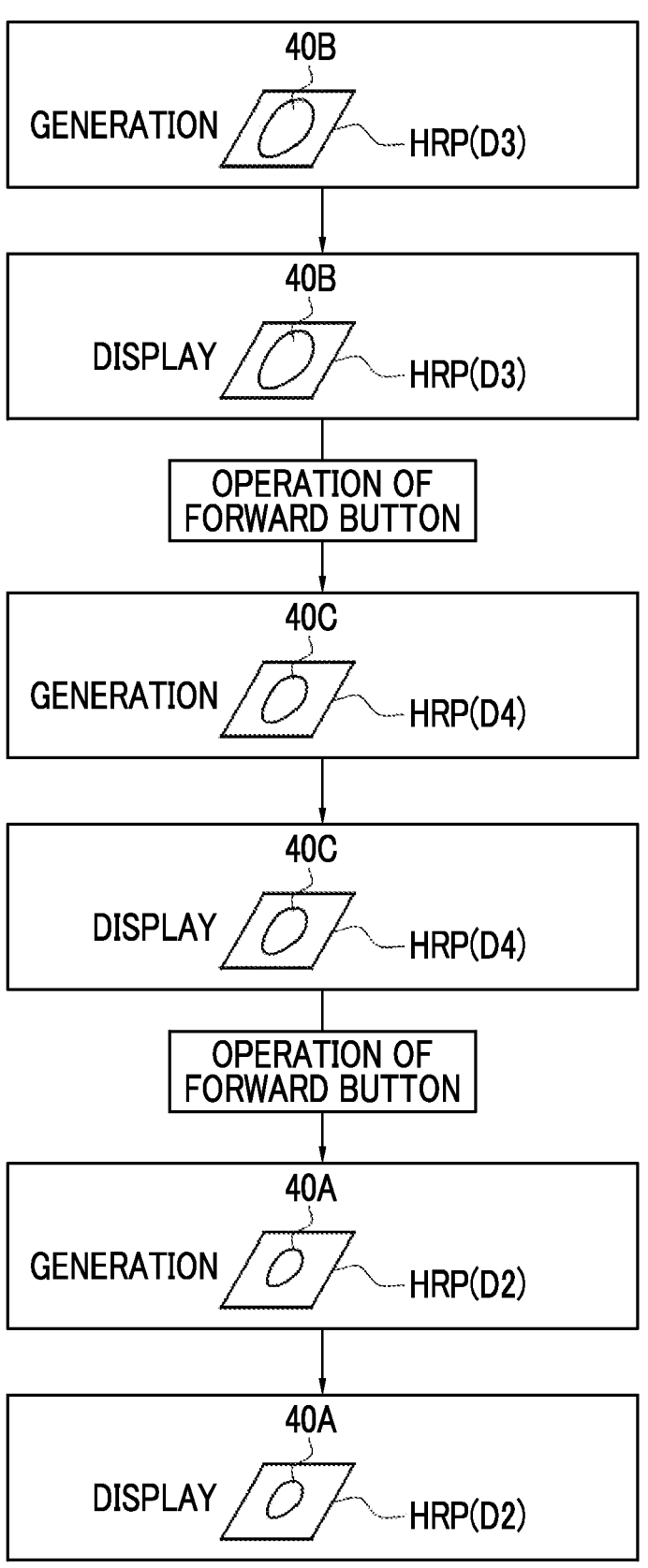
FIG. 20 is a diagram illustrating an aspect in which the high-resolution partial image is generated and displayed whenever a forward button is operated.
Figure 21:
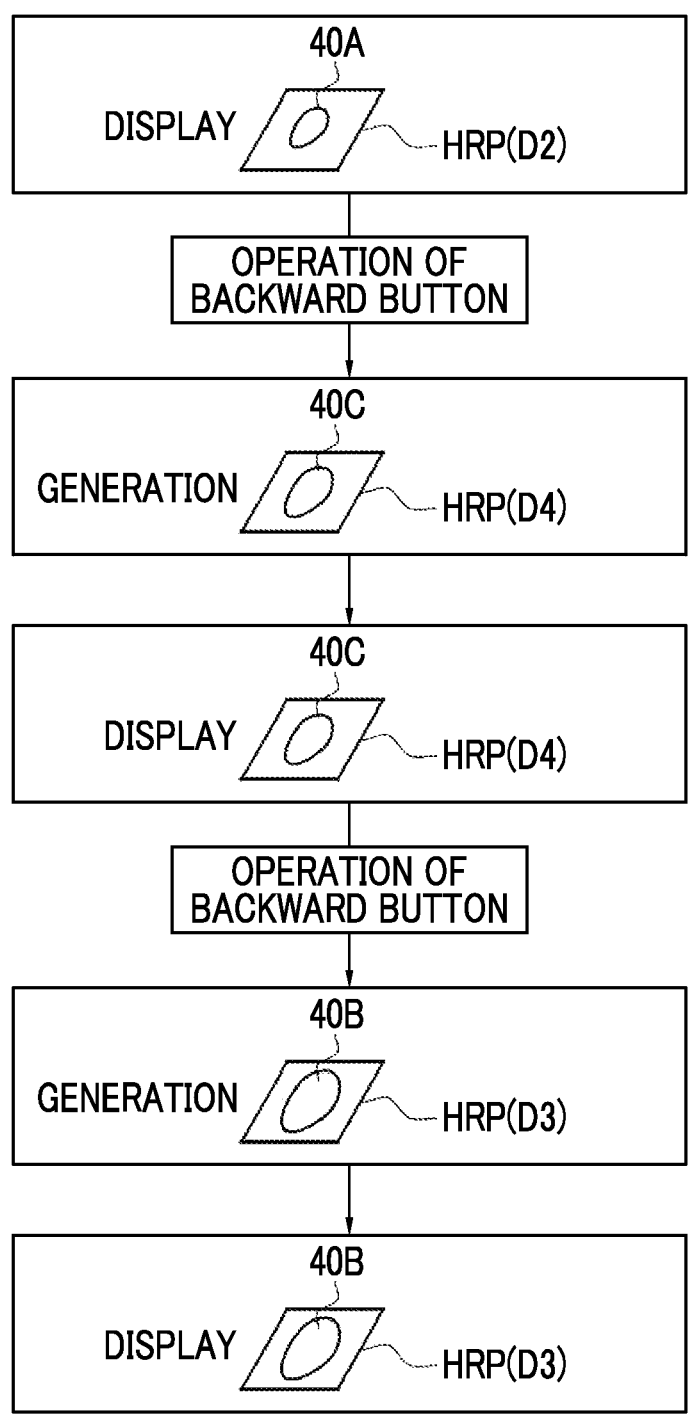
FIG. 21 is a diagram illustrating an aspect in which the high-resolution partial image is generated and displayed whenever a backward button is operated.

As illustrated in FIGS. 20 and 21, whenever the instruction receiving unit 32 receives the instruction to switch the display of the high-resolution partial image HRP input by the operation of the forward button 72B and the backward button 73B, the resolution enhancement unit 35 generates the high-resolution partial image HRP.

FIG. 20 illustrates a case in which the forward button 72B is operated in the example illustrated in FIG. 12 and FIG. 17. In this case, the display control unit 36 first displays the high-resolution partial image HRP(D3) on the screen 71. In a case in which the forward button 72B is operated in a state in which the high-resolution partial image HRP(D3) is displayed, the resolution enhancement unit 35 generates the high-resolution partial image HRP(D4), and the display control unit 36 displays the high-resolution partial image HRP(D4) on the screen 71. In a case in which the forward button 72B is operated in a state in which the high-resolution partial image HRP(D4) is displayed, the resolution enhancement unit 35 generates the high-resolution partial image HRP(D2), and the display control unit 36 displays the high-resolution partial image HRP(D2) on the screen 71.

FIG. 21 illustrates a case in which the backward button 73B is operated in a state in which the high-resolution partial image HRP(D2) is displayed. In this case, the resolution enhancement unit 35 generates the high-resolution partial image HRP(D4), and the display control unit 36 displays the high-resolution partial image HRP(D4) on the screen 71. In a case in which the backward button 73B is operated in a state in which the high-resolution partial image HRP(D4) is displayed, the resolution enhancement unit 35 generates the high-resolution partial image HRP(D3), and the display control unit 36 displays the high-resolution partial image HRP(D3) on the screen 71.

Figure 22:
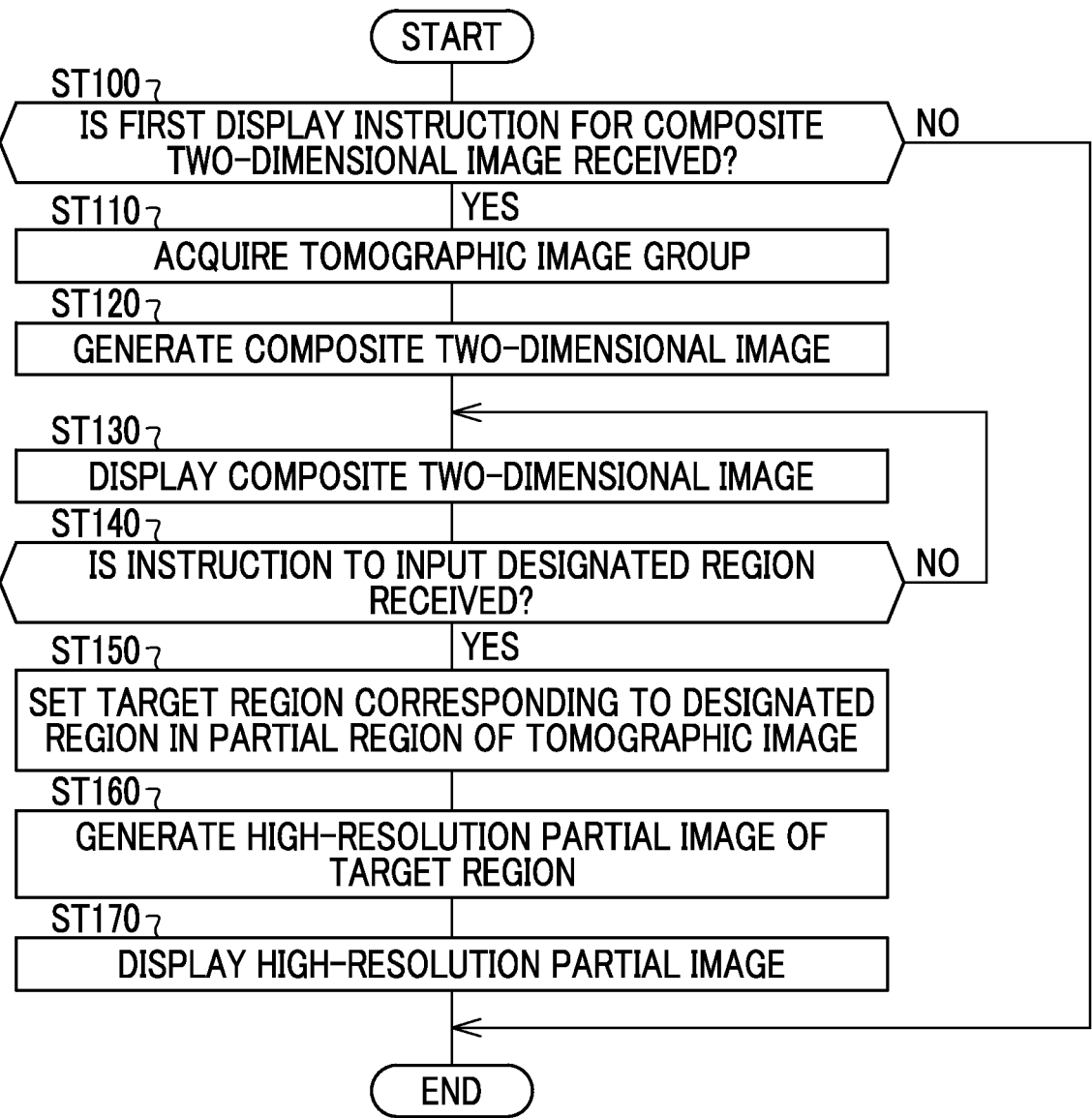
FIG. 22 is a diagram illustrating a processing procedure of the image processing device.

Next, the operation of the above-mentioned configuration will be described with reference to a flowchart illustrated in FIG. 22. First, in a case in which the image processing program 22 is started in the image processing device 4, as illustrated in FIG. 4, the CPU 21 of the image processing device 4 functions as the image acquisition unit 30, the combination unit 31, the instruction receiving unit 32, the structure-of-interest detection unit 33, the target region setting unit 34, the resolution enhancement unit 35, and the display control unit 36.

Under the control of the display control unit 36, the screen 45 illustrated in FIG. 9 is displayed on the display 24. In a case in which the file path of the desired tomographic image group SD is input to the input box 46 and the display button 48 is operated on the screen 45, the instruction receiving unit 32 receives the first display instruction for the composite two-dimensional image CG1 (YES in Step ST100).

A request to distribute the tomographic image group SD whose file path has been input to the input box 46 is transmitted from the image acquisition unit 30 to the console 2 or the image storage system 3. Then, the image acquisition unit 30 acquires the tomographic image group SD distributed from the console 2 or the image storage system 3 in response to the distribution request (Step ST110). The tomographic image group SD is output from the image acquisition unit 30 to the combination unit 31.

As illustrated in FIGS. 7 and 8, the combination unit 31 generates the composite two-dimensional image CG1 from the tomographic image group SD (Step ST120). Alternatively, the image storage system 3 may be provided with the combination unit 31, and the image acquisition unit 30 may acquire the composite two-dimensional image CG1 distributed from the image storage system 3. The composite two-dimensional image CG1 is output from the combination unit 31 to the display control unit 36. Then, as illustrated in FIG. 9, the screen 49 including the composite two-dimensional image CG1 is displayed on the display 24 under the control of the display control unit 36 (Step ST130). The user interprets the composite two-dimensional image CG1 through the screen 49.

In a case in which the user places the cursor 50 of the mouse on a portion of interest of the breast M in the composite two-dimensional image CG1 and clicks the portion of interest on the screen 49, the instruction receiving unit 32 receives the instruction to input the designated region SR (YES in Step ST140). In this way, the designated region SR is set on the composite two-dimensional image CG1. The information of the designated region SR is output from the instruction receiving unit 32 to the target region setting unit 34.

As illustrated in FIG. 12 or FIG. 13, the target region setting unit 34 sets the target region OR corresponding to the designated region SR in the tomographic images Dj (Step ST150). The image of the target region OR is output from the target region setting unit 34 to the resolution enhancement unit 35.

As illustrated in FIG. 14 and the like, the resolution enhancement unit 35 increases the resolution of the image of the target region OR to generate the high-resolution partial image HRP of the target region OR (Step ST160). The high-resolution partial image HRP is output from the resolution enhancement unit 35 to the display control unit 36.

Under the control of the display control unit 36, the screen 71 illustrated in FIG. 19 including the composite two-dimensional image CG1, the tomographic image Dj, and the high-resolution partial image HRP is displayed on the display 24 (Step ST170). The user interprets the tomographic image Dj and the high-resolution partial image HRP in detail through the screen 71.

As described above, the CPU 21 of the image processing device 4 functions as the image acquisition unit 30, the instruction receiving unit 32, the target region setting unit 34, the resolution enhancement unit 35, and the display control unit 36. The image acquisition unit 30 acquires a plurality of tomographic images Dj which have the first resolution and indicate a plurality of tomographic planes of the breast M, respectively. The instruction receiving unit 32 receives the instruction to input the designated region SR as the operation instruction related to interpretation from the user. In a case in which the instruction receiving unit 32 receives the instruction to input the designated region SR, the target region setting unit 34 sets a region, which is a portion of the tomographic image Dj and corresponds to the designated region SR, as the target region OR. The resolution enhancement unit 35 performs a process of converting the resolution to the second resolution higher than the first resolution only on the target region OR to generate the high-resolution partial image HRP of the target region OR. The display control unit 36 displays the high-resolution partial image HRP.

As described above, the region whose resolution is to be increased is limited to the target region OR. Therefore, it is possible to shorten the time required for displaying the high-resolution tomographic image (in this case, the high-resolution partial image HRP) as compared to a case in which the resolution of the entire region of the tomographic image Dj is increased. In addition, since it is not necessary to increase the resolution of the tomographic images Dj of all of the tomographic planes in advance, a problem, such as pressure on the storage capacity of the storage 23, does not occur.

The instruction receiving unit 32 receives the instruction to input the designated region SR in the composite two-dimensional image CG1 as an example of the two-dimensional image which is the projection image of the breast M as the operation instruction related to interpretation. The target region setting unit 34 sets the target region OR on the basis of the designated region SR. Therefore, it is possible to precisely increase the resolution of the portion that the user is interested in.

As illustrated in FIG. 12, the structure-of-interest detection unit 33 performs the process of detecting the structure of interest 40 in the designated region SR. In a case in which the structure of interest 40 is detected, the target region setting unit 34 sets a region including the structure of interest 40 in the tomographic image Dj as the target region OR.

Therefore, it is possible to increase the resolution of the structure of interest 40 and to interpret the structure of interest 40 in detail.

On the other hand, as illustrated in FIG. 13, in a case in which the structure-of-interest detection unit 33 does not detect the structure of interest 40, a region corresponding to the designated region SR in the tomographic image Dj of a predetermined set tomographic plane is set as the target region OR. Therefore, it is also possible to respond to, for example, a case in which the structure of interest 40 is not recognized, but the user clicks a portion of the breast M in the composite two-dimensional image CG1 to look at the portion for checking. In addition, in a case in which the structure-of-interest detection unit 33 does not detect the structure of interest 40, the setting of the target region OR, the generation of the high-resolution partial image HRP, and the display of the high-resolution partial image HRP may not be performed, and a display screen of a warning message "The structure of interest is not found. Please designate another portion." may be displayed on the screen 49.

As illustrated in FIG. 11, the structure of interest 40 is at least one of the tumor 51, the spicula 52, the calcification 53, or the linear structure 54. A few percent of the tumor 51 is likely to be malignant. The spicula 52 is a finding characteristic of hard cancer or invasive lobular cancer. The calcification 53 is likely to become cancerous. Lesions, such as the tumor 51, the spicula 52, and the calcification 53, are likely to occur in the linear structure 54. Therefore, in a case in which at least one of the tumor 51, the spicula 52, the calcification 53, or the linear structure 54 is set as the structure of interest 40, it is possible to more efficiently perform interpretation.

As illustrated in FIG. 14, the resolution enhancement unit 35 applies the super-resolution method to the process of converting the first resolution into the second resolution. Therefore, it is possible to perform interpretation with an image in which details are expressed in very high definition.

As illustrated in FIGS. 20 and 21, in a case in which the target region setting unit 34 sets a plurality of target regions OR and the resolution enhancement unit 35 generates a plurality of high-resolution partial images HRP, the high-resolution partial image HRP is generated whenever the second display instruction for the high-resolution partial images HRP (the operation of the forward button 72B and the backward button 73B) is received from the user. It is possible to generate the high-resolution partial image HRP in a relatively short time. Therefore, there is no concern that a time lag which is long enough to cause a problem in practice will occur between the input of the second display instruction for the high-resolution partial image HRP to the actual display of the high-resolution partial image HRP.

As illustrated on the screen 71 of FIG. 19, the display control unit 36 displays the high-resolution partial image HRP separately from the tomographic image Dj in which the target region OR is set. Therefore, it is possible to observe in detail the target region OR in the high-resolution partial image HRP while observing the entire breast M in the tomographic image Dj.

As illustrated in FIGS. 17 and 18, the display control unit 36 displays the high-resolution partial image HRP prior to the tomographic image Dj in which the target region OR is not set. Therefore, the high-resolution partial image HRP having a higher priority can be read first.

As illustrated in FIGS. 17 and 18, in a case in which the target region setting unit 34 sets a plurality of target regions OR and the resolution enhancement unit 35 generates a plurality of high-resolution partial images HRP, the display control unit 36 first displays one high-resolution partial image HRP that satisfies the predetermined display condition 66A or 66B among the plurality of high-resolution partial images HRP. Therefore, the high-resolution partial image HRP that is considered to be most important can be interpreted first.

In the description of FIG. 14, in the case of FIG. 12, the high-resolution partial images HRP of all of the target regions OR of the tomographic images D2, D3, and D4 are generated. However, the present disclosure is not limited thereto. Only the high-resolution partial image HRP(D3) of the target region OR of the tomographic image D3 including the structure of interest 40B having the largest area may be generated. Similarly, in the case of FIG. 13, the high-resolution partial images HRP of all of the target regions OR of the tomographic images DC, DC−1, and DC+1 are generated. However, the present disclosure is not limited thereto. For example, only the high-resolution partial image HRP(DC) of the target region OR of the tomographic image DC of the central tomographic plane may be generated.

A plurality of radiation sources 16 may be arranged at each radiation source position Si, and radiation may be sequentially emitted from the plurality of radiation sources 16 to capture the projection images G1.

Figure 23:
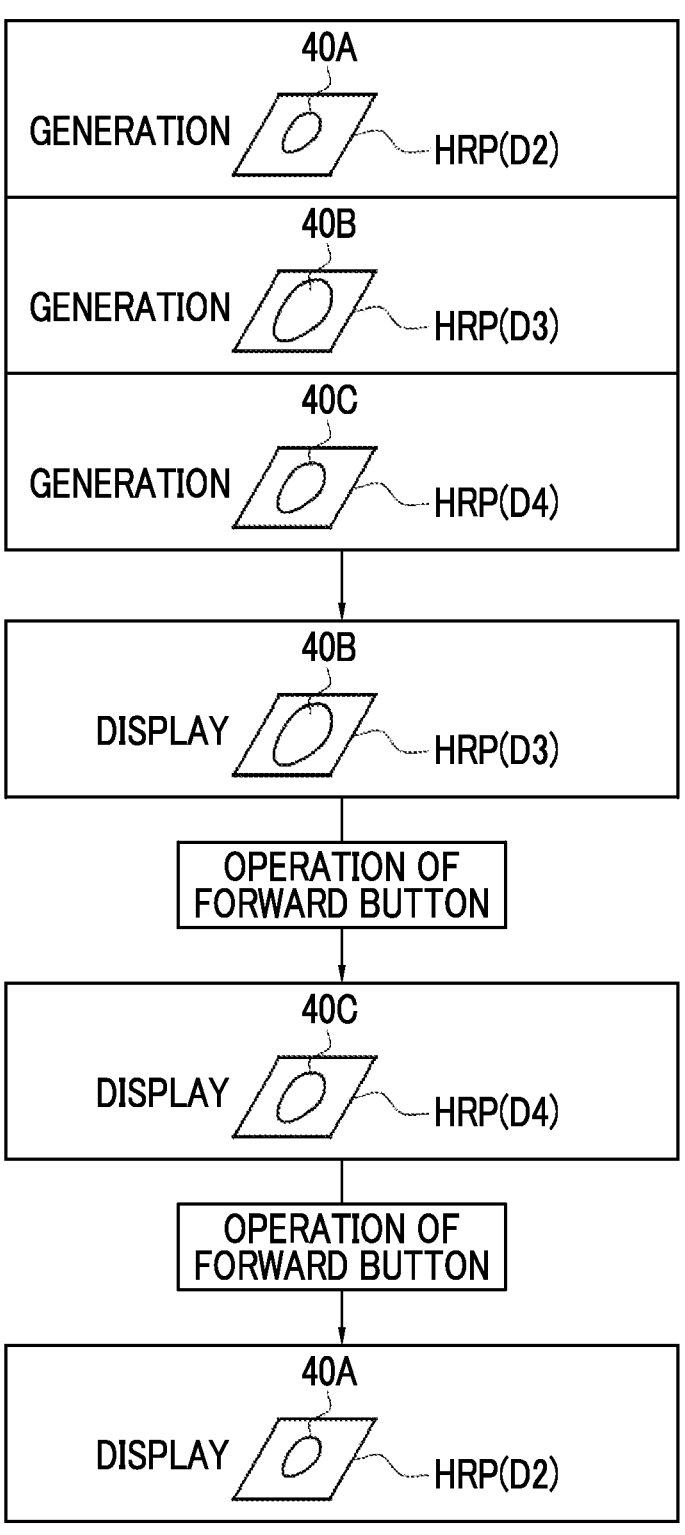
FIG. 23 is a diagram illustrating an aspect in which all of the high-resolution partial images are generated and displayed in advance.

In addition, as illustrated in FIG. 23, the high-resolution partial image HRP of each of the plurality of target regions OR may be generated before the second display instruction for the high-resolution partial image HRP is received, instead of whenever the second display instruction for the high-resolution partial image HRP is received from the user.

FIG. 23 illustrates a case in which the forward button 72B is operated in the example illustrated in FIG. 12 and FIG. 17. In this case, the resolution enhancement unit 35 generates the high-resolution partial images HRP(D2), HRP(D3), and HRP(D4) in advance. The display control unit 36 first displays the high-resolution partial image HRP(D3) on the screen 71. In a case in which the forward button 72B is operated in a state in which the high-resolution partial image HRP(D3) is displayed, the display control unit 36 displays the high-resolution partial image HRP(D4) on the screen 71. In a case in which the forward button 72B is operated in a state in which the high-resolution partial image HRP(D4) is displayed, the display control unit 36 displays the high-resolution partial image HRP(D2) on the screen 71.

According to the aspect illustrated in FIG. 23, since all of the high-resolution partial images HRP are generated first, it takes little time from the input of the second display instruction for the high-resolution partial image HRP to the actual display of the high-resolution partial image HRP. In addition, since the amount of data in the high-resolution partial image HRP is smaller than that in the image obtained by increasing the resolution of the entire region of the tomographic image Dj, there is no concern that pressure will be applied to the storage capacity of the storage 23. Further, FIG. 23 illustrates a case in which this aspect is applied to the examples illustrated in FIGS. 12 and 17. However, this aspect may be applied to the examples illustrated in FIGS. 13 and 18 to generate the high-resolution partial images HRP(DC), HRP(DC−1), and HRP(DC+1) in advance.

Figure 24:
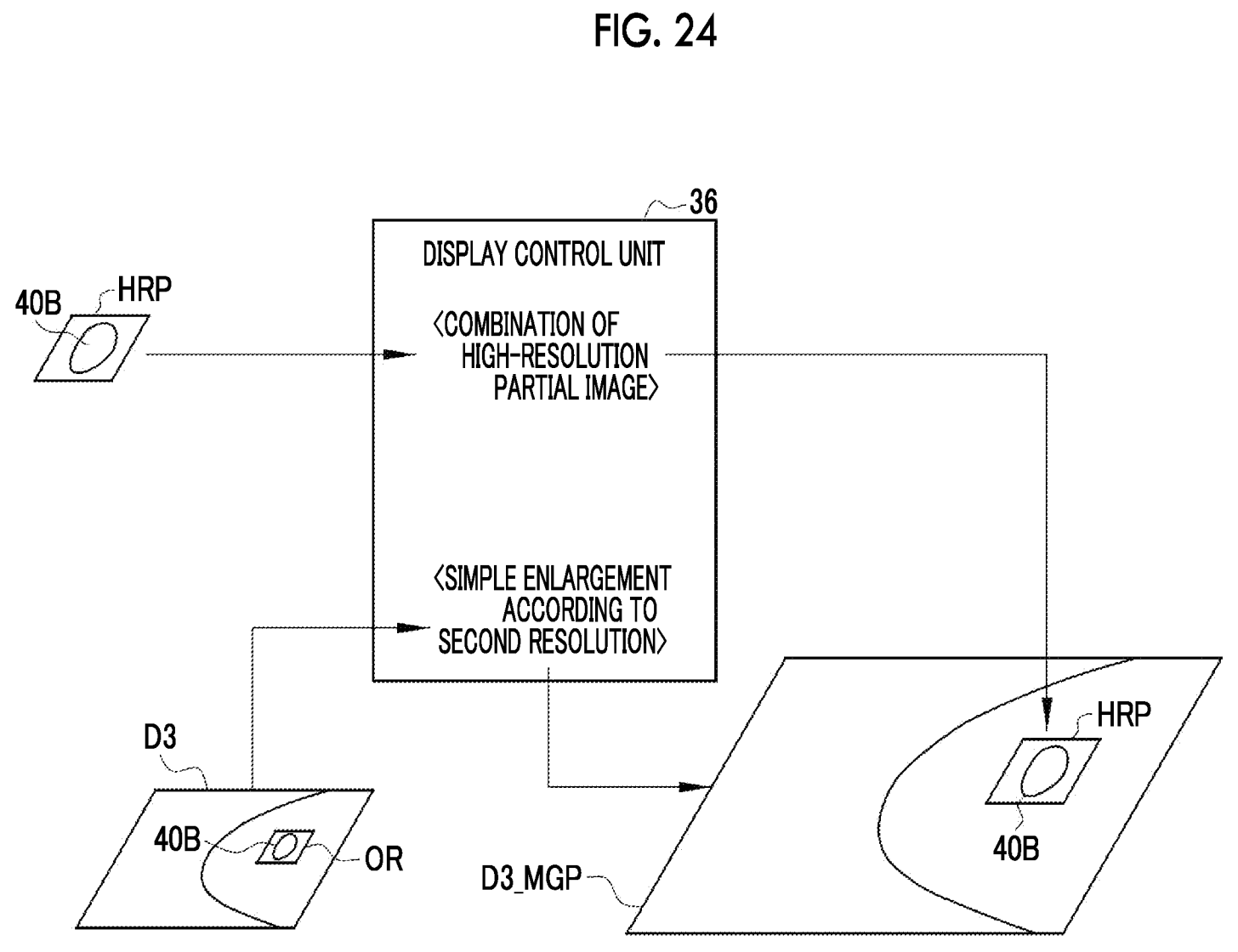

Display aspects illustrated in FIGS. 24 and 25 may be adopted.

As illustrated in FIG. 24, the display control unit 36 simply enlarges a region other than the target region OR in the tomographic image Dj, in which the target region OR is set, in accordance with the second resolution to convert the tomographic image Dj into a simply enlarged tomographic image Dj_MGP. Then, the display control unit 36 combines the high-resolution partial image HRP with the simply enlarged tomographic image Dj_MGP. FIG. 24 illustrates an aspect in which the high-resolution partial image HRP including the structure of interest 40B is combined with the simply enlarged tomographic image D3_MGP of the tomographic image D3 in which the target region OR is set in the structure of interest 40B.

In this case, the display control unit 36 displays a screen 81 illustrated in FIG. 25 on the display 24 instead of the screen 71 illustrated in FIG. 19. The composite two-dimensional image CG1 and the simply enlarged tomographic image Dj_MGP with which the high-resolution partial image HRP has been combined are displayed side by side on the screen 81. FIG. 25 illustrates an example in which the simply enlarged tomographic image D3_MGP is displayed.

According to the display aspects illustrated in FIGS. 24 and 25, it is possible to observe the high-resolution partial image HRP on the tomographic image Dj. In addition, similarly to the screen 71 illustrated in FIG. 19, the high-resolution partial image HRP may also be displayed side by side on the screen 81.

On the screen 49 illustrated in FIG. 10, the user places the cursor 50 on the portion of interest and clicks the portion of interest to designate the designated region SR. After that, various processes are performed to generate the high-resolution partial image HRP, and the high-resolution partial image HRP is displayed on the screen 71 illustrated in FIG. 19. However, the present disclosure is not limited thereto. Aspects illustrated in FIGS. 26 to 28 may be adopted.

Figure 26:
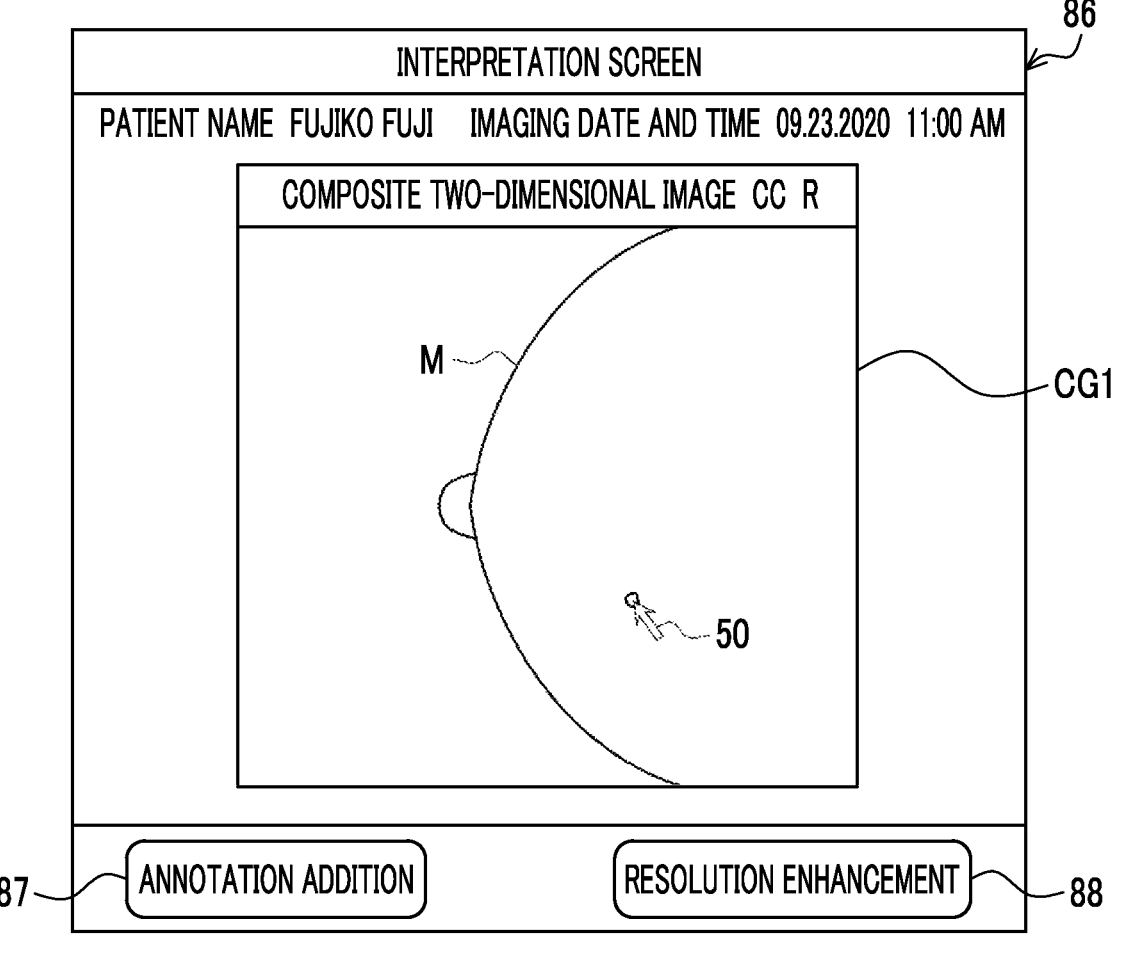
FIG. 26 is a diagram illustrating a screen that is provided with an annotation addition button and a resolution enhancement button.
Figure 27:
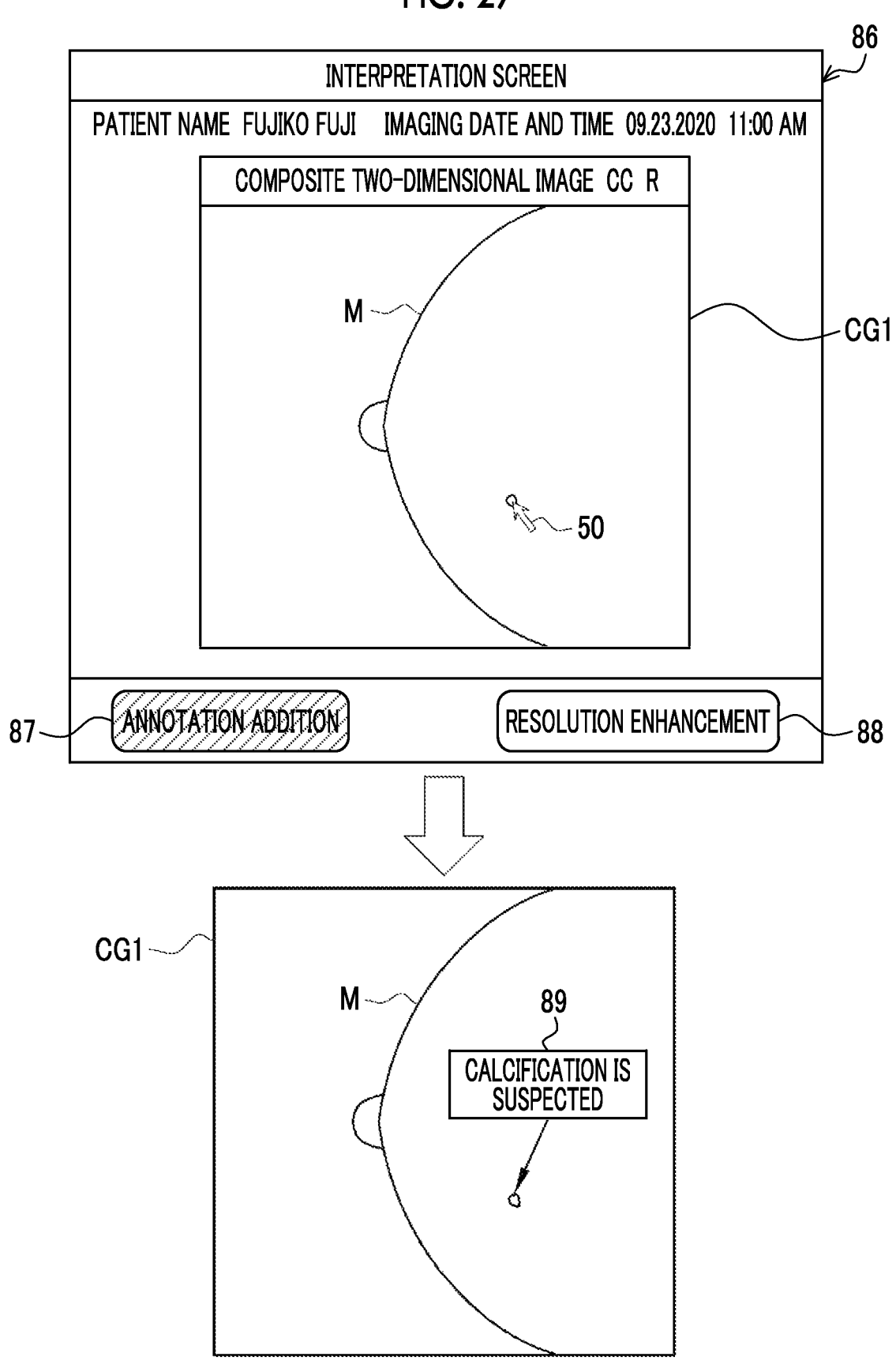
FIG. 27 is a diagram illustrating an aspect in which the annotation addition button is selected and an annotation is added to a portion on which a cursor is placed and which is clicked.

In FIG. 26, a screen 86 that is displayed on the display 24 instead of the screen 49 illustrated in FIG. 10 is provided with an annotation addition button 87 and a resolution enhancement button 88. In a case in which the user wants to add an annotation 89 to a portion of interest of the breast M included in the composite two-dimensional image CG1, the user places the cursor 50 of the mouse on the portion of interest, clicks the portion of interest, and then selects the annotation addition button 87 as illustrated in FIG. 27. In this way, it is possible to add the annotation 89 to the portion where the cursor 50 is placed.

Figure 28:
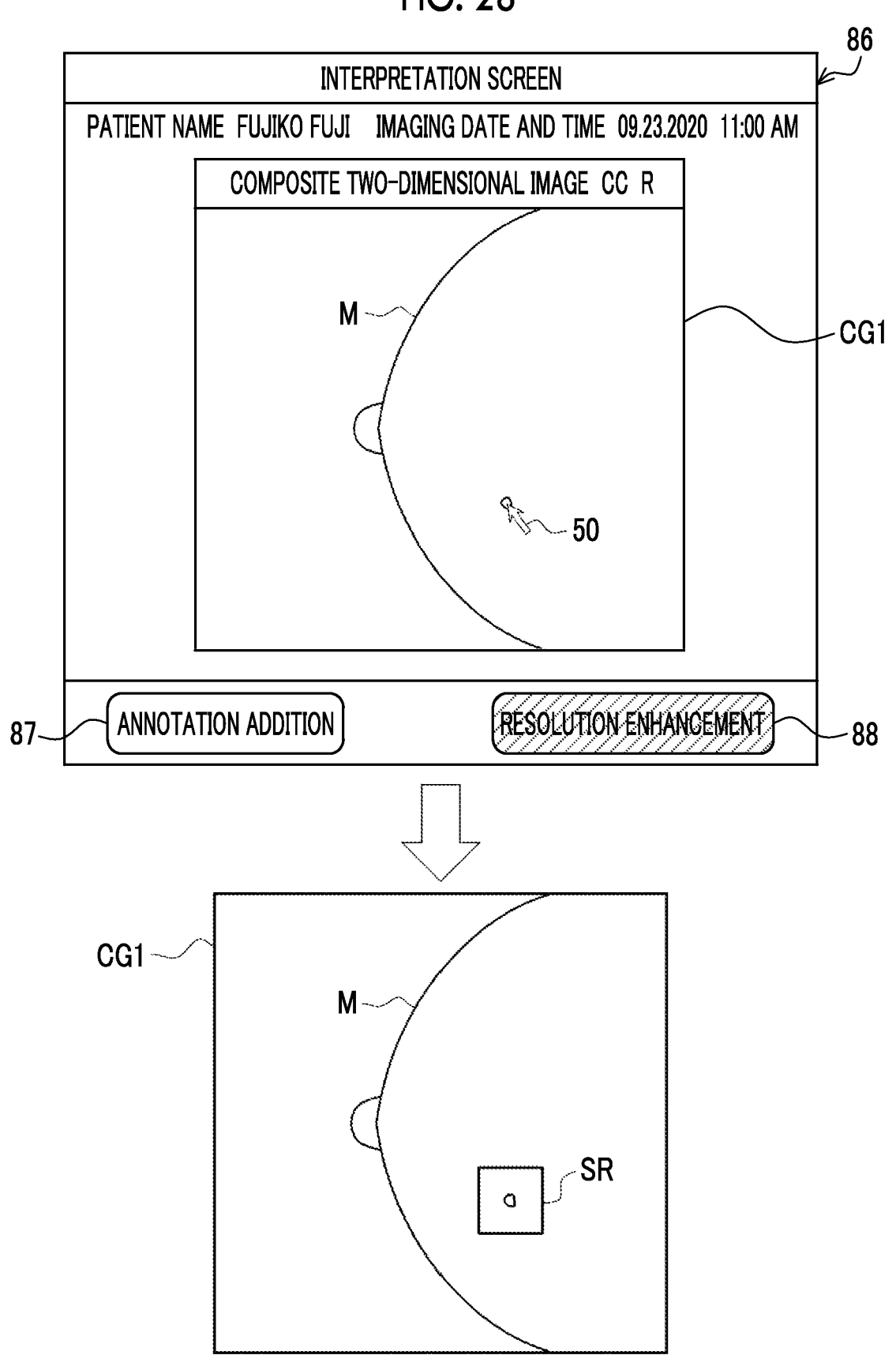
FIG. 28 is a diagram illustrating an aspect in which the resolution enhancement button is selected and the designated region is set in a portion on which the cursor is placed and which is clicked.

Meanwhile, in a case in which the user wants to see the high-resolution partial image HRP of the portion of interest, the user places the cursor 50 of the mouse on the portion of interest, clicks the portion of interest, and then selects the resolution enhancement button 88 as illustrated in FIG. 28. Then, the designated region SR is set in the portion on which the cursor 50 is placed, and then various processes are performed to display the high-resolution partial image HRP. The resolution enhancement button 88 is an example of a "graphical user interface" according to the technology of the present disclosure. In addition, the operation of the resolution enhancement button 88 is an example of the "second display instruction for the high-resolution partial image" according to the technology of the present disclosure.

According to the aspects illustrated in FIGS. 26 to 28, a process, such as the addition of the annotation 89, other than the resolution enhancement can be performed on the portion of interest. The process other than the resolution enhancement is not limited to the addition of the annotation 89 and may be, for example, a process of applying CAD that estimates the type of lesion to the portion on which the cursor 50 is placed and which is clicked. In addition, the order of the clicking of the mouse and the selection of the resolution enhancement button 88 may be reversed. That is, after the resolution enhancement button 88 is selected, the cursor 50 of the mouse may be placed on the portion of interest, and the portion of interest may be clicked.

Second Embodiment

In the first embodiment, the target region OR is set on the basis of the designated region SR set by the operation of the user. However, the present disclosure is not limited thereto. A second embodiment illustrated in FIGS. 29 to 31 may be adopted.

Figure 29:
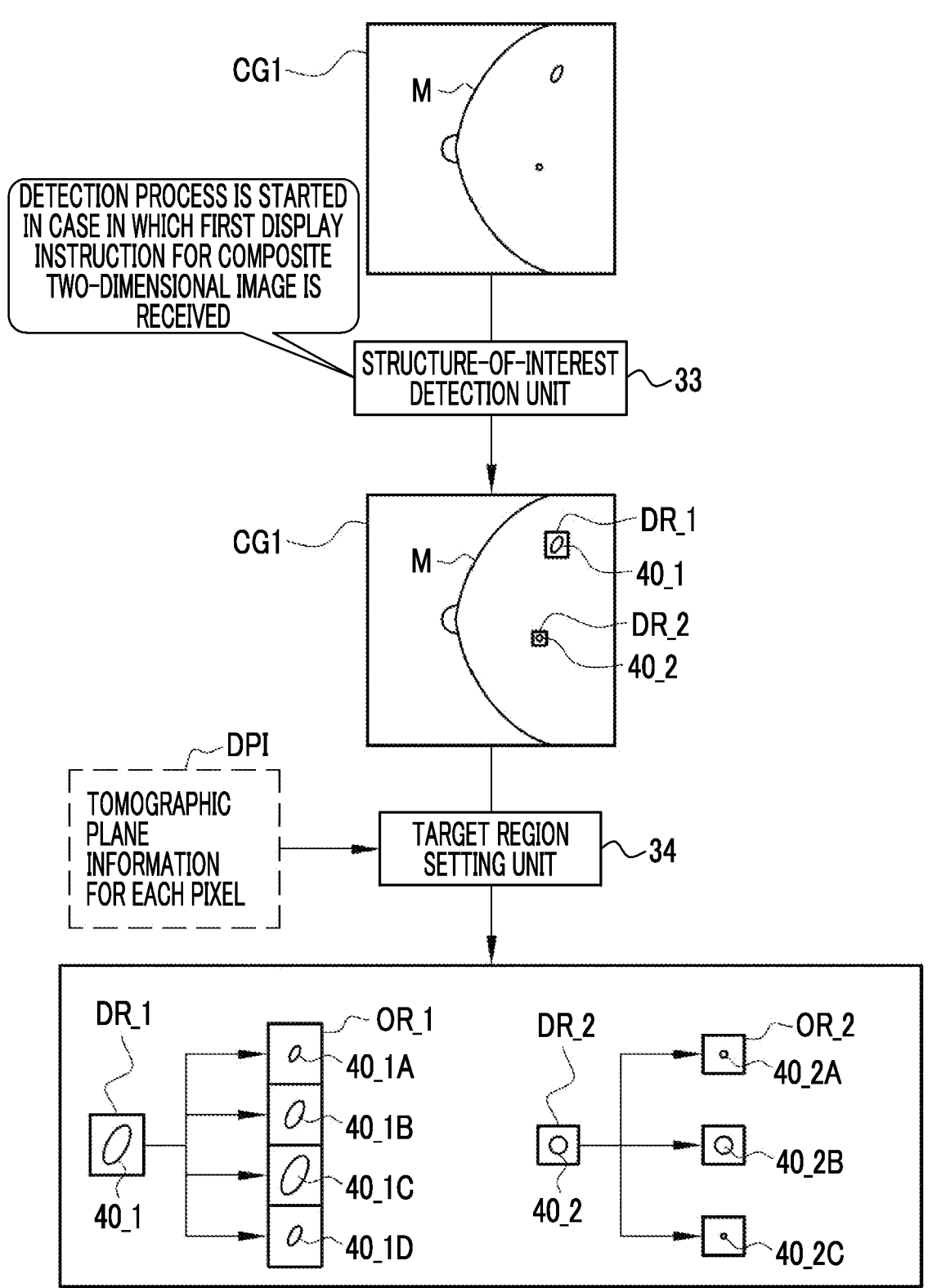
FIG. 29 is a diagram illustrating a process of a structure-of-interest detection unit and a target region setting unit according to a second embodiment.

In FIG. 29, in a case in which the instruction receiving unit 32 receives the first display instruction for the composite two-dimensional image CG1, the structure-of-interest detection unit 33 performs a process of detecting the structure of interest 40 on the composite two-dimensional image CG1. The first display instruction for the composite two-dimensional image CG1 is the operation of the display button 48 as illustrated in FIG. 9. Further, the structures of interest 40 detected by the structure-of-interest detection unit 33 are the tumor 51, the spicula 52, the calcification 53, and the linear structure 54 as in the first embodiment. In addition, the process of detecting the structure of interest 40 may be performed on the simple two-dimensional image Gc0 instead of the composite two-dimensional image CG1.

The structure-of-interest detection unit 33 sets a detection region DR including the detected structure of interest 40. The detection region DR is a rectangle which surrounds the detected structure of interest 40 and has a center matched with the center of the structure of interest 40. The detection region DR has a size that is slightly larger than that of the structure of interest 40, for example, a size that is about 20% to 30% larger than that of the structure of interest 40. The structure-of-interest detection unit 33 outputs image information of the detection region DR to the target region setting unit 34. FIG. 29 illustrates a case in which structures of interest 40_1 and 40_2 are detected, a detection region DR_1 is set for the structure of interest 40_1, and a detection region DR_2 is set for the structure of interest 40_2. In addition, the detection region DR may have a predetermined size similarly to the designated region SR. Further, the detection region DR may have any shape, such as a circular shape, and may have a size corresponding to the type of the structure of interest 40. Furthermore, the detection region DR may be a region that is surrounded by the contour of the structure of interest 40 detected by the structure-of-interest detection unit 33.

The target region setting unit 34 sets the region including the detected structure of interest 40, that is, the detection region DR as the target region OR in the tomographic image Dj. Specifically, as in the first embodiment, the target region setting unit 34 specifies the tomographic plane in which the structure of interest 40 is present with reference to the tomographic plane information DPI and sets the same region as the detection region DR of the tomographic image Dj of the specified tomographic plane as the target region OR. FIG. 29 illustrates a case in which target regions OR_1 of structures of interest 40_1A, 40_1B, 40_1C, and 40_1D corresponding to the structure of interest 40_1 are set for the detection region DR_1 of the structure of interest 40_1 and target regions OR_2 of structures of interest 40_2A, 40_2B, and 40_2C corresponding to the structure of interest 40_2 are set for the detection region DR_2 of the structure of interest 40_2. In addition, a region which is not the same region as the detection region DR and is surrounded by the contour of the structure of interest 40 may be set as the target region OR.

Figure 30:
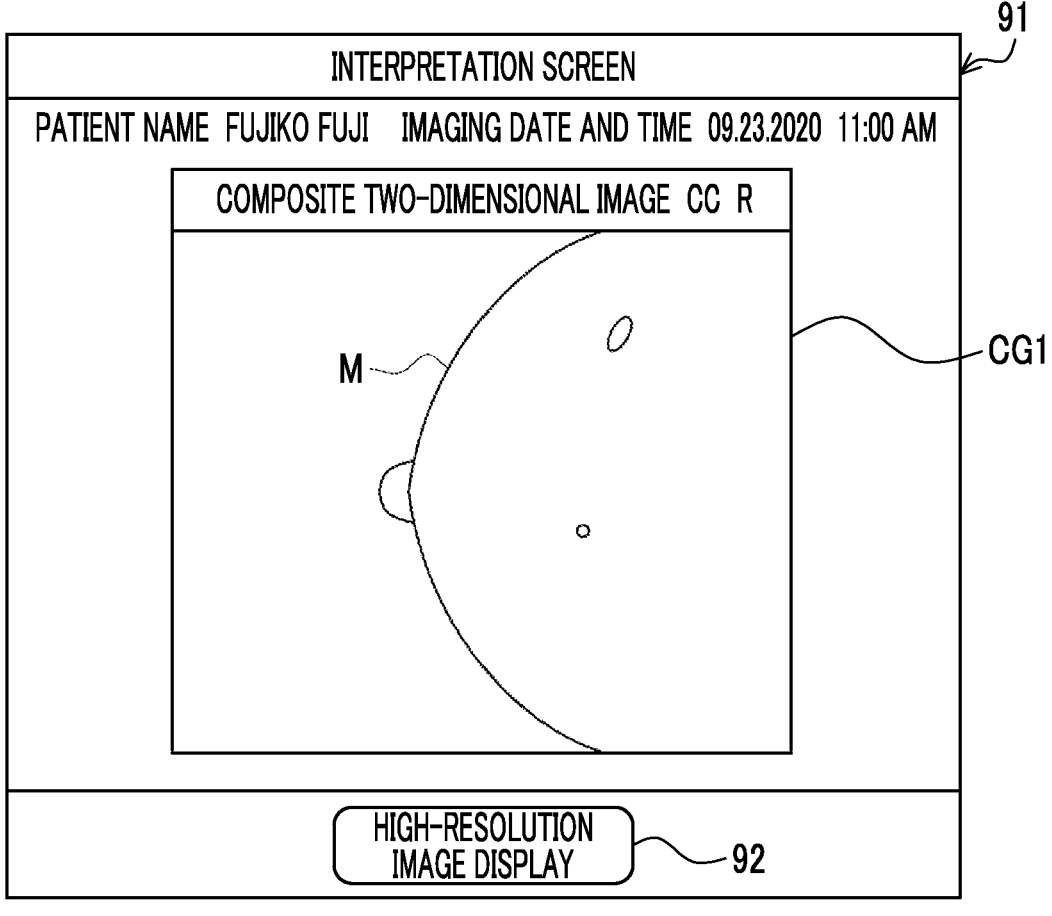
FIG. 30 is a diagram illustrating a screen according to the second embodiment which includes a composite two-dimensional image and is provided with a high-resolution image display button.

In the second embodiment, as illustrated in FIG. 30, a screen 91 including the composite two-dimensional image CG1 is provided with a high-resolution image display button 92. In a case in which the high-resolution image display button 92 is selected, the screen 71 including the high-resolution partial image HRP illustrated in FIG. 19 or the screen 81 including the simply enlarged tomographic image Dj_MGP with which the high-resolution partial image HRP illustrated in FIG. 25 has been combined is displayed. That is, the high-resolution image display button 92 is an example of the "graphical user interface" according to the technology of the present disclosure. In addition, the operation of the high-resolution image display button 92 is an example of the "second display instruction for the high-resolution partial image" according to the technology of the present disclosure. Further, the high-resolution partial image HRP displayed first is, for example, the high-resolution partial image HRP in which the structure of interest 40 has the largest area, as in the case of FIG. 17.

Figure 31:
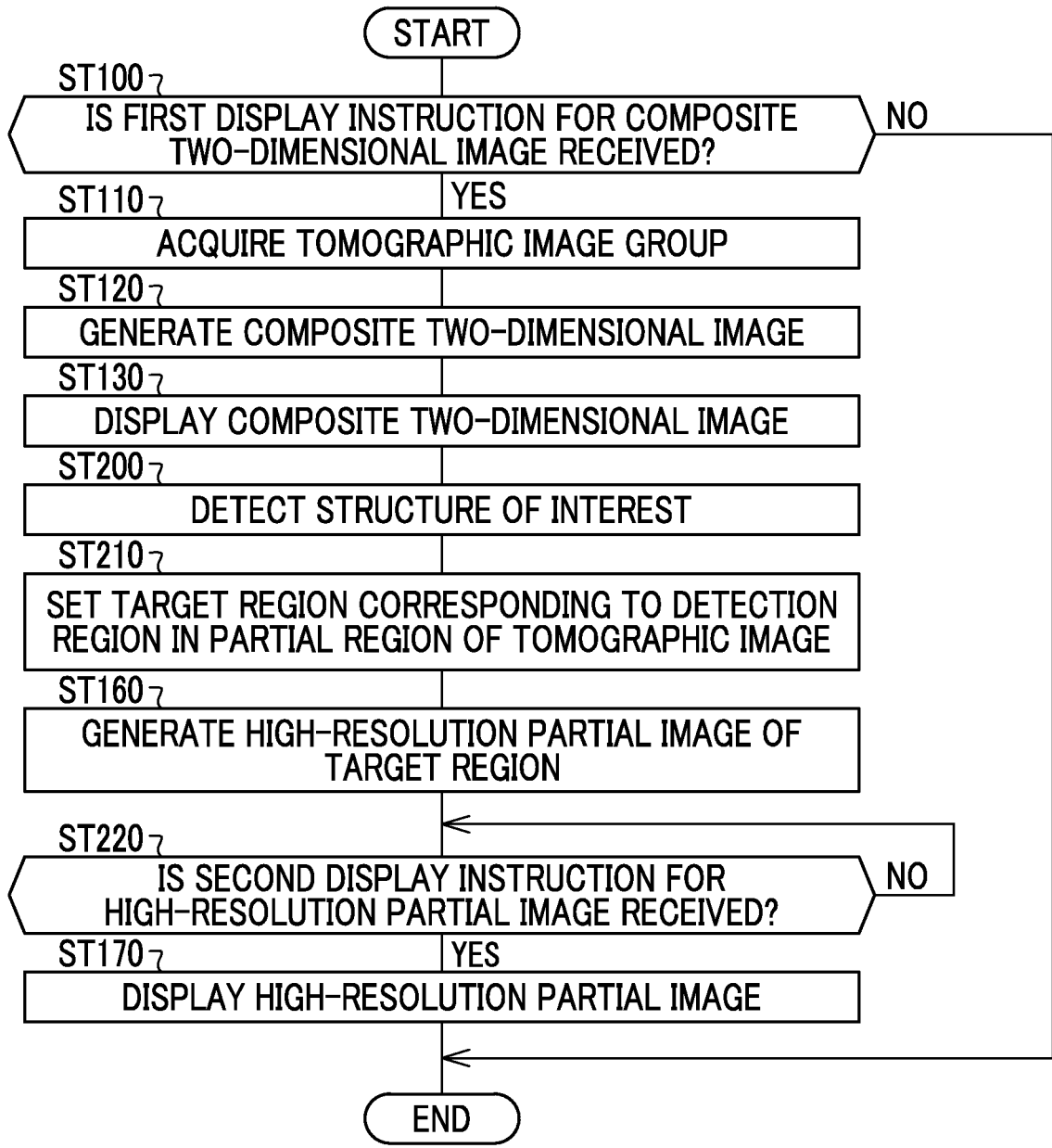
FIG. 31 is a diagram illustrating a processing procedure of an image processing device according to the second embodiment.

FIG. 31 is a flowchart illustrating the operation of the second embodiment. As in the first embodiment, the instruction receiving unit 32 receives the first display instruction for the composite two-dimensional image CG1 (YES in Step ST100), and the image acquisition unit 30 acquires the tomographic image group SD (Step ST110). Then, the combination unit 31 generates the composite two-dimensional image CG1 (Step ST120), and the screen 91 including the composite two-dimensional image CG1 is displayed on the display 24 under the control of the display control unit 36 (Step ST130).

During the interpretation of the composite two-dimensional image CG1 on the screen 91, the structure-of-interest detection unit 33 performs the process of detecting the structure of interest 40 on the composite two-dimensional image CG1 as illustrated in FIG. 29 (Step ST200). Then, the target region setting unit 34 sets the target region OR corresponding to the detection region DR including the structure of interest 40 in the tomographic image Dj (Step ST210). Then, the resolution enhancement unit 35 increases the resolution of the image of the target region OR to generate the high-resolution partial image HRP of the target region OR (Step ST160).

In a case in which the high-resolution image display button 92 is selected on the screen 91, the instruction receiving unit 32 receives the second display instruction for the high-resolution partial image HRP (YES in Step ST220). Then, under the control of the display control unit 36, the high-resolution partial image HRP is displayed on the display 24 (Step ST170).

As described above, in the second embodiment, in a case in which the first display instruction for the composite two-dimensional image CG1 is received, the structure-of-interest detection unit 33 performs the process of detecting the structure of interest 40 on the composite two-dimensional image CG1. Then, the target region setting unit 34 sets a region including the detected structure of interest 40 as the target region OR in the tomographic image Dj. Therefore, it is possible to display the high-resolution partial image HRP without performing the operation of placing the cursor 50 of the mouse on the portion of interest and clicking the portion of interest unlike the first embodiment. In addition, in a case in which the detection accuracy of the structure-of-interest detection unit 33 is high, the structure of interest 40 that may be overlooked by the user's eyes can be thoroughly detected, and the high-resolution partial image HRP can be generated and displayed.

Further, the high-resolution image display button 92 may not be provided, and the high-resolution partial image HRP may be displayed on the screen 91 as soon as the high-resolution partial image HRP is generated. In addition, the process of detecting the structure of interest 40 may be performed in a case in which the high-resolution image display button 92 is selected.

A configuration may be used in which the user can select between the aspect according to the first embodiment in which the user performs the operation of placing the cursor 50 of the mouse on the portion of interest and clicking the portion of interest and the aspect according to the second embodiment.

In a case in which the simple two-dimensional image Gc0 is used instead of the composite two-dimensional image CG1, the tomographic plane information DPI may be generated by the following method. That is, the simple two-dimensional image Gc0 and the tomographic images Dj are divided into a plurality of regions (for example, regions having a size of 2 pixels×2 pixels). Then, the correlation between the region of the simple two-dimensional image Gc0 and the region of each of the tomographic images Dj is calculated, and the tomographic plane of the tomographic image Dj having a region with a relatively large correlation is recorded as the tomographic plane corresponding to the pixels in the region of the simple two-dimensional image Gc0. Similarly, in the case of the composite two-dimensional image CG1, the above-described method for calculating the correlation may be applied to generate the tomographic plane information DPI.

The operation of the forward button 72A and the backward button 73A is given as an example of the operation for sequentially displaying the tomographic images Dj of a plurality of tomographic planes one by one. The operation of the forward button 72B and the backward button 73B is given as an example of the operation for sequentially displaying a plurality of high-resolution partial images HRP one by one. However, the present disclosure is not limited thereto. The tomographic images Dj of the plurality of tomographic planes and/or the plurality of high-resolution partial images HRP may be sequentially displayed in response to the operation of a scroll button of the mouse.

In each of the above-described embodiments, the tomographic images Dj obtained by the tomosynthesis imaging are given as an example. However, the present disclosure is not limited thereto. For example, tomographic images obtained by computed tomography (CT), positron emission tomography (PET), single photon emission computed tomography (SPECT), or magnetic resonance imaging (MRI) may be used.

In each of the above-described embodiments, for example, the following various processors can be used as the hardware structure of processing units performing various processes, such as the image acquisition unit 30, the combination unit 31, the instruction receiving unit 32, the structure-of-interest detection unit 33, the target region setting unit 34, the resolution enhancement unit 35, and the display control unit 36. The various processors include, for example, the CPU 21 which is a general-purpose processor executing software (image processing program 22) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other as appropriate. In addition, the present disclosure is not limited to each of the above-described embodiments, and various configurations can be used without departing from the gist of the present disclosure.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, in the content described and illustrated above, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference in the specification to the same extent as each individual document, each patent application, and each technical standard are specifically and individually stated to be incorporated by reference.

What is claimed is:

1. An image processing device comprising:
   a processor; and
   a memory that is connected to or provided in the processor,
   wherein the processor acquires a plurality of tomographic images which indicate a plurality of tomographic planes of an object, respectively, and have a first resolution, receives an instruction from a user to input a designated region in a two-dimensional image which is a projection image of the object, as an operation instruction related to interpretation,
   detects a structure of interest in the designated region,
   sets a plurality of target regions by setting, in each of the plurality of tomographic images, as a target region corresponding to the designated region, a region including the structure of interest,
   performs a process of converting a resolution into a second resolution higher than the first resolution only on each of the plurality of target regions to generate a plurality of high-resolution partial images, and
   displays the plurality of high-resolution partial images,
   wherein the processor determines a display order of the plurality of high-resolution partial images based on an area of the structure of interest depicted in each of the plurality of high-resolution partial images, and displays the plurality of high-resolution partial images one by one in descending order of the area whenever a display instruction is received from the user,
   wherein the plurality of tomographic images are obtained by tomosynthesis imaging which irradiates the object with radiation at a plurality of different irradiation angles, and
   wherein the two-dimensional image is either a simple two-dimensional image obtained by simple imaging which emits the radiation, with a radiation source facing a radiation detector, or a composite two-dimensional image which is a pseudo simple two-dimensional image obtained by combining the plurality of tomographic images using a composite image generation technique.

2. The image processing device according to claim 1, wherein the object is a breast, and
   the structure of interest is at least one of a tumor, a spicula, a calcification, or a linear structure.

3. The image processing device according to claim 1, wherein the processor displays the plurality of high-resolution partial images separately from the plurality of tomographic images in which the plurality of target regions are set.

4. The image processing device according to claim 1, wherein the processor combines each of the plurality of high-resolution partial images with an enlarged image obtained by simply enlarging a region other than the target region in each of the plurality of tomographic images, in which the plurality of target regions are set, according to the second resolution and displays the enlarged image.

5. The image processing device according to claim 1, wherein the processor displays the plurality of high-resolution partial images prior to the plurality of tomographic images in which the plurality of target regions are not set.

6. The image processing device according to claim 1, wherein, in a case in which the display instruction is received through a graphical user interface after the operation instruction is received, the processor generates and displays each of the plurality of high-resolution partial images.

7. A method for operating an image processing device, the method comprising:
   acquiring a plurality of tomographic images which indicate a plurality of tomographic planes of an object, respectively, and have a first resolution;

receiving an instruction from a user to input a designated region in a two-dimensional image which is a projection image of the object, as an operation instruction related to interpretation;

detecting a structure of interest in the designated region;

setting a plurality of target regions by setting, in each of the plurality of tomographic images, as a target region corresponding to the designated region, a region including the structure of interest;

performing a process of converting a resolution into a second resolution higher than the first resolution only on each of the plurality of target regions to generate a plurality of high-resolution partial images; and displaying the plurality of high-resolution partial images, wherein a display order of the plurality of high-resolution partial images is determined based on an area of the structure of interest depicted in each of the plurality of high-resolution partial images, and the plurality of high-resolution partial images are displayed one by one in descending order of the area whenever a display instruction is received from the user, wherein the plurality of tomographic images are obtained by tomosynthesis imaging which irradiates the object with radiation at a plurality of different irradiation angles, and wherein the two-dimensional image is either a simple two-dimensional image obtained by simple imaging which emits the radiation, with a radiation source facing a radiation detector, or a composite two-dimensional image which is a pseudo simple two-dimensional image obtained by combining the plurality of tomographic images using a composite image generation technique.

8. A non-transitory computer-readable storage medium storing a program for operating an image processing device, the program causing a computer to execute a process comprising:

acquiring a plurality of tomographic images which indicate a plurality of tomographic planes of an object, respectively, and have a first resolution;

receiving an instruction from a user to input a designated region in a two-dimensional image which is a projection image of the object, as an operation instruction related to interpretation;

detecting a structure of interest in the designated region;

setting a plurality of target regions by setting, in each of the plurality of tomographic images, as a target region corresponding to the designated region, a region including the structure of interest;

performing a process of converting a resolution into a second resolution higher than the first resolution only on each of the plurality of target regions to generate a plurality of high-resolution partial images; and displaying the plurality of high-resolution partial images, wherein a display order of the plurality of high-resolution partial images is determined based on an area of the structure of interest depicted in each of the plurality of high-resolution partial images, and the plurality of high-resolution partial images are displayed one by one in descending order of the area whenever a display instruction is received from the user, wherein the plurality of tomographic images are obtained by tomosynthesis imaging which irradiates the object with radiation at a plurality of different irradiation angles, and wherein the two-dimensional image is either a simple two-dimensional image obtained by simple imaging which emits the radiation, with a radiation source facing a radiation detector, or a composite two-dimensional image which is a pseudo simple two-dimensional image obtained by combining the plurality of tomographic images using a composite image generation technique.

9. An image processing device comprising:

a processor; and a memory that is connected to or provided in the processor, wherein the processor acquires a plurality of tomographic images which indicate a plurality of tomographic planes of an object, respectively, and have a first resolution, receives an instruction from a user to input a designated region in a two-dimensional image which is a projection image of the object, as an operation instruction related to interpretation, detects a structure of interest in the designated region, sets a plurality of target regions by setting, in each of the plurality of tomographic images, as a target region corresponding to the designated region, a region including the structure of interest, performs a process of converting a resolution into a second resolution higher than the first resolution only on each of the plurality of target regions to generate a plurality of high-resolution partial images, and displays the plurality of high-resolution partial images, wherein a display order of the plurality of high-resolution partial images is determined based on an area of the structure of interest depicted in each of the plurality of high-resolution partial images, and the plurality of high-resolution partial images are displayed one by one in descending order of the area whenever a display instruction is received from the user, wherein the plurality of tomographic images are obtained by tomosynthesis imaging which irradiates the object with radiation at a plurality of different irradiation angles, and wherein the two-dimensional image is a composite two-dimensional image generated by adding or averaging the plurality of tomographic images in a depth direction in which the plurality of tomographic planes are arranged.

* * * * *